(12) United States Patent
Hashimoto

(10) Patent No.: US 11,980,595 B2
(45) Date of Patent: May 14, 2024

(54) PREVENTIVE OR THERAPEUTIC AGENT AND PHARMACEUTICAL COMPOSITION FOR INFLAMMATORY DISEASES OR BONE DISEASES

(71) Applicant: National University Corporation Chiba University, Chiba (JP)

(72) Inventor: Kenji Hashimoto, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 16/969,713

(22) PCT Filed: Feb. 14, 2019

(86) PCT No.: PCT/JP2019/005415
§ 371 (c)(1),
(2) Date: Aug. 13, 2020

(87) PCT Pub. No.: WO2019/160057
PCT Pub. Date: Aug. 22, 2019

(65) Prior Publication Data
US 2021/0000762 A1    Jan. 7, 2021

(30) Foreign Application Priority Data

Feb. 15, 2018  (JP) .............................. JP2018-025170
Jun. 27, 2018  (JP) .............................. JP2018-121858

(51) Int. Cl.
*A61K 31/135*    (2006.01)
*A61P 1/00*       (2006.01)
*A61P 19/10*      (2006.01)

(52) U.S. Cl.
CPC ............ *A61K 31/135* (2013.01); *A61P 19/10* (2018.01)

(58) Field of Classification Search
CPC ................................ A61K 31/135; A61P 1/00
See application file for complete search history.

(56) References Cited

U.S. PATENT DOCUMENTS

| | | |
|---|---|---|
| 3,254,124 A | 5/1966 | Stevens |
| 4,670,459 A | 6/1987 | Sjoerdsma |
| 5,543,434 A | 8/1996 | Weg |
| 5,679,714 A | 10/1997 | Weg |
| 5,989,582 A | 11/1999 | Weg |
| 6,040,479 A | 3/2000 | Steiner et al. |
| 6,248,789 B1 | 6/2001 | Weg |
| 6,743,949 B2 | 6/2004 | Russo et al. |
| 6,962,151 B1 | 11/2005 | Knoch et al. |
| 7,001,609 B1 | 2/2006 | Matson et al. |
| 7,044,125 B2 | 5/2006 | Vedrine et al. |
| 7,090,830 B2 | 8/2006 | Hale et al. |
| 7,273,889 B2 | 9/2007 | Mermelstein et al. |
| 7,713,440 B2 | 5/2010 | Anderson |
| 7,973,043 B2 | 7/2011 | Migaly |
| 8,785,500 B2 | 7/2014 | Charney et al. |
| 9,539,220 B2 | 1/2017 | Charney et al. |
| 9,592,207 B2 | 3/2017 | Charney et al. |
| 9,610,259 B2 | 4/2017 | Erickson et al. |
| 9,872,841 B2 | 1/2018 | Hashimoto |
| 9,918,993 B2 | 3/2018 | Berdahl et al. |
| 10,232,117 B2 | 3/2019 | Halseth |
| 10,252,982 B2 | 4/2019 | Nivorozhkin et al. |
| 10,406,121 B2 | 9/2019 | Hashimoto |
| 10,441,544 B2 | 10/2019 | Glue et al. |
| 10,478,405 B2 | 11/2019 | Charney et al. |

(Continued)

FOREIGN PATENT DOCUMENTS

| | | |
|---|---|---|
| DE | 2062 620 A1 | 7/1971 |
| EP | 3085366 A1 | 10/2016 |

(Continued)

OTHER PUBLICATIONS

Rodan et al. Science 2000, 289 (5484), 1508-1514.*
Webb Biochemical Pharmacology 2014, 87, 121-130.*
Carroll, K. M. & Onken, L. S., "Behavioral Therapies for Drug Abuse," Am J Psychiatry; 162:1452-1460 (2005).
Kawasaki, C. et al., "Ketamine isomers suppress superantigen-induced proinflammatory cytokine production in human whole blood," Can J Anesth, 48(8):819-823 (2001).

(Continued)

*Primary Examiner* — Irina Neagu
(74) *Attorney, Agent, or Firm* — COOLEY LLP

(57) ABSTRACT

This preventive or therapeutic agent for inflammatory diseases or bone diseases, and this pharmaceutical composition for preventing or treating inflammatory diseases or bone diseases include, as effective components, a compound represented by formula (1) or a pharmaceutically acceptable salt thereof.

[Formula 1]

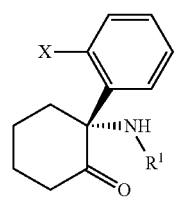

(1)

[In formula (1), X is a hydrogen atom, a halogen atom, or a $C_1$-$C_{10}$ alkyl group that may be substituted; $R^1$ is a $C_1$-$C_{10}$ alkyl group that may be substituted, a $C_1$-$C_{10}$ alkenyl group that may be substituted, or a $C_6$-$C_{14}$ aryl group that may be substituted; and one or more hydrogen atoms may be substituted with deuterium atoms.]

14 Claims, 13 Drawing Sheets

(56) References Cited

U.S. PATENT DOCUMENTS

| | | | |
|---|---|---|---|
| 10,683,262 B2 | 6/2020 | Xiang et al. |
| 10,744,094 B2 | 8/2020 | Glue et al. |
| 10,815,196 B2 | 10/2020 | Chen et al. |
| 10,836,714 B2 | 11/2020 | Xiang et al. |
| 10,869,838 B2 | 12/2020 | Glue et al. |
| 10,881,665 B2 | 1/2021 | Javitt |
| 10,973,780 B2 | 4/2021 | Becker et al. |
| 11,007,200 B2 | 5/2021 | Godek et al. |
| 11,045,424 B2 | 6/2021 | Glue et al. |
| 11,103,499 B2 | 8/2021 | Vepachedu et al. |
| 11,191,734 B2 | 12/2021 | Tang et al. |
| 11,207,279 B2 | 12/2021 | Hashimoto |
| 11,253,487 B2 | 2/2022 | Kagan et al. |
| 11,286,230 B2 | 3/2022 | Toupy et al. |
| 11,426,367 B2 | 8/2022 | Witkin et al. |
| 2004/0248964 A1 | 12/2004 | Crooks et al. |
| 2008/0268071 A1 | 10/2008 | Gant et al. |
| 2012/0225949 A1 | 9/2012 | Papalos |
| 2013/0236573 A1 | 9/2013 | Singh et al. |
| 2014/0057988 A1 | 2/2014 | Weg |
| 2014/0093592 A1 | 4/2014 | Singh et al. |
| 2014/0274981 A1 | 9/2014 | Basstanie et al. |
| 2014/0275276 A1 | 9/2014 | Basstanie et al. |
| 2014/0275277 A1 | 9/2014 | Basstanie et al. |
| 2014/0275278 A1 | 9/2014 | Basstanie et al. |
| 2015/0056308 A1 | 2/2015 | Charney et al. |
| 2015/0057306 A1 | 2/2015 | Fava et al. |
| 2015/0196501 A1 | 7/2015 | Erickson et al. |
| 2016/0045455 A1 | 2/2016 | Drevets et al. |
| 2016/0067196 A1 | 3/2016 | Charney et al. |
| 2016/0175266 A1 | 6/2016 | Mermelstein et al. |
| 2016/0220513 A1* | 8/2016 | Hashimoto ............ A61P 25/00 |
| 2019/0060254 A1 | 2/2019 | Sherman et al. |
| 2019/0083420 A1 | 3/2019 | Wainer et al. |
| 2019/0117591 A1 | 4/2019 | Basstanie et al. |
| 2019/0343781 A1 | 11/2019 | Hashimoto |
| 2019/0350879 A1 | 11/2019 | Jay |
| 2020/0000748 A1 | 1/2020 | Kagan et al. |
| 2020/0069674 A1 | 3/2020 | Vepachedu et al. |
| 2020/0121619 A1 | 4/2020 | Rey |
| 2020/0147005 A1 | 5/2020 | Kagan et al. |
| 2020/0261442 A1 | 8/2020 | Vepachedu |
| 2020/0297734 A1 | 9/2020 | Saadeh |
| 2020/0360307 A1 | 11/2020 | Denny et al. |
| 2020/0360308 A1 | 11/2020 | Becker et al. |
| 2020/0405663 A1 | 12/2020 | Hashimoto |
| 2021/0032194 A1 | 2/2021 | Kandula |
| 2021/0196654 A1 | 7/2021 | Gershon et al. |
| 2021/0251969 A1 | 8/2021 | Abdallah et al. |
| 2021/0259993 A1 | 8/2021 | Witkin et al. |
| 2021/0378989 A1 | 12/2021 | Kagan |
| 2022/0041540 A1 | 2/2022 | Kruegel |
| 2022/0071929 A1 | 3/2022 | Hashimoto |
| 2022/0110889 A1 | 4/2022 | Hashimoto |
| 2022/0119338 A1 | 4/2022 | Lin et al. |
| 2022/0151955 A1 | 5/2022 | Wolfson et al. |
| 2022/0347124 A1 | 11/2022 | Witkin et al. |

FOREIGN PATENT DOCUMENTS

| | | |
|---|---|---|
| EP | 3130582 A1 | 2/2017 |
| EP | 3263108 A1 | 1/2018 |
| EP | 3689340 A1 | 8/2020 |
| GB | 1 330 878 A | 9/1973 |
| JP | 2008509137 A | 3/2008 |
| JP | 4401613 B2 | 1/2010 |
| JP | 2010525081 A | 7/2010 |
| JP | 2017519723 A | 7/2017 |
| WO | WO 01/062932 A1 | 8/2001 |
| WO | WO 01/098265 A2 | 12/2001 |
| WO | WO 2004/028522 | 4/2004 |
| WO | WO-2006019962 A1 | 2/2006 |
| WO | WO 2007/038949 A1 | 4/2007 |
| WO | WO 2007/111880 A2 | 10/2007 |
| WO | WO-2008134525 A1 | 11/2008 |
| WO | WO 2011/020061 A2 | 2/2011 |
| WO | WO 2013/138322 A1 | 9/2013 |
| WO | WO-2015037248 A1 | 3/2015 |
| WO | WO 2015/051259 A1 | 4/2015 |
| WO | WO 2016/073653 A1 | 5/2016 |
| WO | WO 2016/170124 A2 | 10/2016 |
| WO | WO 2016/180984 A1 | 11/2016 |
| WO | WO 2016/186968 A1 | 11/2016 |
| WO | WO 2017/087691 A1 | 5/2017 |
| WO | WO-2017180589 A1 | 10/2017 |
| WO | WO 2019/065900 A1 | 4/2019 |
| WO | WO 2019/160057 A1 | 8/2019 |
| WO | WO 2019/169165 A1 | 9/2019 |
| WO | WO 2019/213551 A1 | 11/2019 |
| WO | WO 2019/243791 A1 | 12/2019 |
| WO | WO 2020/138491 A1 | 7/2020 |
| WO | WO 2020/198039 A1 | 10/2020 |
| WO | WO 2020/212510 A1 | 10/2020 |
| WO | WO 2021/121366 A1 | 6/2021 |
| WO | WO 2021/134086 A1 | 7/2021 |
| WO | WO 2021/137147 A1 | 7/2021 |
| WO | WO 2021/150985 A1 | 7/2021 |
| WO | WO 2021/195627 A1 | 9/2021 |
| WO | WO 2021/207359 A1 | 10/2021 |
| WO | WO 2021/231905 A1 | 11/2021 |
| WO | WO 2021/252971 A1 | 12/2021 |
| WO | WO 2021/255737 A1 | 12/2021 |

OTHER PUBLICATIONS

Xiong, Z. et al., "Beneficial effects of (R)-ketamine, but not its metabolite (2R,6R)-hydroxynorketamine, in the depression-like phenotype, inflammatory bone markers, and bone mineral density in a chronic social defeat stress model," Behavioural Brain Research, 368:111904 (2019), 7 pages; https://doi.org/10.1016/j.bbr.2019.111904.

Abbott, A. & Dolgin, E., "Leading Alzheimer's theory survives drug failure," Nature, 540(7631):15-16 (2016).

Abi-Saab, W. M. et al., "The NMDA Antagonist Model for Schizophrenia: Promise and Pitfalls," Pharmacopsychiat. 31(Suppl):104-109 (1998).

Ashry, E. E. et al., "Protective Effect of Ketamine against Acetic Acid-Induced Ulcerative Colitis in Rats," Pharmacology & Pharmacy, 7:9-18 (2016).

Barch, D. M. & Ceaser, A., "Cognition in schizophrenia: core psychological and neural mechanisms," Trends in Cognitive Sciences, 16(1):27-34 (2012).

Bell, D. S., "The Motivation of Addiction," Acta Neurochir (Wien), 132:185-191 (1995).

Berman, R. M. et al., "Antidepressant Effects of Ketamine in Depressed Patients," Biological Psychiatry, 47:351-354 (2000).

Bloch, M. H. et al., "Effects of Ketamine in Treatment-Refractory Obsessive-Compulsive Disorder," Biol Psychiatry, 72(11):964-970 (2012).

Carlezon, W. A. & Wise, R. A., "Microinjections of phencyclidine (PCP) and related drugs into nucleus accumbens shell potentiate medial forebrain bundle brain stimulation reward," Psychopharmacology, 128:413-420 (1996).

Carlezon, W. A. & Chartoff, E. H., "Intracranial self-stimulation (ICSS) in rodents to study the neurobiology of motivation," Nature Protocols, 2(11):2987-2995 (2007).

Cooper, M. D. et al., "Strategies to mitigate dissociative and psychotomimetic effects of ketamine in the treatment of major depressive episodes: a narrative review," The World Journal of Biological Psychiatry, 18(6):410-423 (2017).

Deneau, G. A. & Seevers, M. H., "Pharmacological Aspects of Drug Dependence," Advances in Pharmacology, 3:267-283 (1964).

Diazgranados, N. et al., "A randomized add-on trial of an N-methyl-D-aspartate antagonist in treatment-resistant bipolar depression," Arch Gen Psychiatry, 67(8):793-802 (2010).

Diazgranados, N. et al., "Rapid Resolution of Suicidal Ideation After a Single Infusion of an N-Methyl-D-Aspartate Antagonist in Patients With Treatment-Resistant Major Depressive Disorder," J Clin Psychiatry, 71(12):1605-1611 (2010).

(56) References Cited

OTHER PUBLICATIONS

Diniz, B. D. et al., "Late-life depression and risk of vascular dementia and Alzheimer's disease: systematic review and meta-analysis of community-based cohort studies," The British Journal of Psychiatry, 202:329-335 (2013).
Domino, E. F., "Taming the ketamine tiger," Anesthesiology, 113(3):678-686 (2010).
Domino, E. F. & Luby, E. D., "Phencyclidine/Schizophrenia: One View Toward the Past, The Other to the Future," Schizophrenia Bulletin, 38(5):914-919 (2012).
Ebert, B. et al., "Norketamine, the main metabolite of ketamine, is a non-competitive NMDA receptor antagonist in the rat cortex and spinal cord," European Journal of Pharmacology, 333:99-104 (1997).
Elvevåg, B. & Goldberg, T. E., "Cognitive Impairment in Schizophrenia Is the Core of the Disorder," Critical Reviews in Neurobiology, 14(1):1-21 (2000).
Erami, E. et al., "Blockade of orexin receptor 1 attenuates the development of morphine tolerance and physical dependence in rats," Pharmacology, Biochemistry and Behavior, 103:212-219 (2012).
Fan, J. -C. et al., "Neuron-protective effect of subanesthestic-dosage ketamine on mice of Parkinson's disease," Asian Pacific Journal of Tropical Medicine, 10(10):1007-1010 (2017).
Feder, A. et al., "Efficacy of Intravenous Ketamine for Treatment of Chronic Posttraumatic Stress Disorder: A Randomized Clinical Trial," JAMA Psychiatry, 71(6):681-688 (2014).
Ferro, M. M. et al., "Neuroprotective effect of ketamine/xylazine on two rat models of Parkinson's disease," Brazilian Journal of Medical and Biological Research, 40:89-96 (2007).
Fidecka, S., "Interactions of Ketamine, Naloxone and Morphine in the Rat," Pol. J. Pharmacol. Pharm., 39:33-40 (1987).
Freo, U. & Ori, C., "Effects of Anesthesia and Recovery from Ketamine Racemate and Enantiomers on Regional Cerebral Glucose Metabolism in Rats," Anesthesiology, 100:1172-1178 (2004).
Frohlich, J. & Van Horn, J. D., "Reviewing the ketamine model for schizophrenia," Journal of Psychopharmacology, 28(4):287-302 (2014). doi: 10.1177/0269881113512909. Epub Nov. 20, 2013; 16 pages.
Fujita, A. et al., "MPTP-induced dopaminergic neurotoxicity in mouse brain is attenuated after subsequent intranasal administration of (R) -ketamine: a role of TrkB signaling," Psychopharmacology, 237:83-92 (2020); doi:10.1007/S00213-019-05346-5, Aug. 15, 2019.
Fukumoto, K. et al., "Antidepressant Potential of (R)-Ketamine in Rodent Models: Comparison with (S)-Ketamine," J Pharmacol Exp Ther, 361:9-16 (2017).
Gastambide, F. et al., "Temporally distinct cognitive effects following acute administration of ketamine and phencyclidine in the rat," European Neuropsychopharmacology, 23:1414-1422 (2013).
Ginski, M. J. & Witkin, J. M., "Sensitive and rapid behavioral differentiation of N-methyl-D-aspartate receptor antagonists," Psychopharmacology, 114:573-582 (1994).
Golden, S. A. et al., "A standardized protocol for repeated social defeat stress in mice," Nature Protocols, 6(8):1183-1191, (2011), including 1 page corrigendum.
Graf, B. M., "Ketamine Has Stereospecific Effects in the Isolated Perfused Guinea Pig Heart," Anesthesiology, 82(6):1426-1437 (1995).
Hachinski, V. et al., "National Institute of Neurological Disorders and Stroke—Canadian Stroke Network Vascular Cognitive Impairment Harmonization Standards," Stroke, 37:2220-2241 (2006).
Han, M. et al., "Intake of 7,8-Dihydroxyflavone During Juvenile and Adolescent Stages Prevents Onset of Psychosis in Adult Offspring After Maternal Immune Activation," Scientific Reports, 6:36087 (2016), 10 pages; doi:10.1038/srep36087.
Hashimoto, K., "Emerging role of glutamate in the pathophysiology of major depressive disorder," Brain Research Reviews, 61:105-123 (2009).
Hashimoto, K. et al., "Reduction of dopamine $D_{2/3}$ receptor binding in the striatum after a single administration of esketamine, but not R-ketamine: a PET study in conscious monkeys," Eur Arch Psychiatry Clin Neurosci, 267:173-176 (2017).
Hashimoto, K. et al., "Phencyclidine-induced cognitive deficits in mice are improved by subsequent subchronic administration of clozapine, but not haloperidol," European Journal of Pharmacology, 519:114-117 (2005).
Hashimoto, K. et al., "Phencyclidine-Induced Cognitive Deficits in Mice are Improved by Subsequent Subchronic Administration of Fluvoxamine: Role of Sigma-1 Receptors," Neuropsychopharmacology, 32:514-521 (2007).
Hashimoto, K. et al., "Phencyclidine-Induced Cognitive Deficits in Mice are Improved by Subsequent Subchronic Administration of the Novel Selective α7 Nicotinic Receptor Agonist SSR180711," Biol Psychiatry, 63:92-97 (2008).
Hatzigiakoumis, D. S. et al., "Anhedonia and substance dependence: clinical correlates and treatment options," Front. Psychiatry, 2(10):1-12 (2011); https://doi.org/10.3389/fpsyt.2011.00010; 12 pages.
Herman, B. H. et al., "The Effects of NMDA Receptor Antagonists and Nitric Oxide Synthase Inhibitors on Opioid Tolerance and Withdrawal Medication Development Issues for Opiate Addiction," Neuropsychopharmacology, 13(4):269-293 (1995).
Higgins, G. A. & Sellers, E. M., "Antagonist-Precipitated Opioid Withdrawal in Rats: Evidence for Dissociations Between Physical and Motivational Signs," Pharmacology Biochemistry and Behavior, 48(1):1-8 (1994).
Higgins, G. A. et al., "The NMDA Antagonist Dizocilpine (MK801) Attenuates Motivational as well as Somatic Aspects of Naloxone Precipitated Opioid Withdrawal," Life Sciences, 50:PL-167-PL-172 (1992).
Hillhouse, T. M. et al., "Dissociable effects of the noncompetitive NMDA receptor antagonists ketamine and MK-801 on intracranial self-stimulation in rats," Psychopharmacology, 231:2705-2716 (2014).
Hillhouse, T. M. & Porter, J. H., "Ketamine, but not MK-801, produces antidepressant-like effects in rats responding on a differential-reinforcement-of-low- rate operant schedule," Behavioural Pharmacology, 25:80-91 (2014).
Huhn, A. S. et al., Evidence of anhedonia and differential reward processing in prefrontal cortex among post-withdrawal patients with prescription opiate dependence, Brain Research Bulletin, 123:102-109 (2016).
Irwin, S. A. et al., "Daily Oral Ketamine for the Treatment of Depression and Anxiety in Patients Receiving Hospice Care: A 28-Day Open-Label Proof-of-Concept Trial," Journal of Palliative Medicine, 16(8):958-965 (2013).
Jackson-Lewis, V. & Przedborski, S., "Protocol for the MPTP mouse model of Parkinson's disease," Nature Protocols, 2(1):141-151 (2007).
Javitt, D. C. & Zukin, S. R., "Recent Advances in the Phencyclidine Model of Schizophrenia," Am J Psychiatry, 148:1301-1308 (1991).
Ji, D. et al., "NMDA Receptor in Nucleus Accumbens is Implicated in Morphine Withdrawal in Rats," Neorochemical Research, 29(11):2113-2120 (2004).
Johnson, K. M., "Phencyclidine: it ain't excitin', but it sure is toxic," Amino Acids, 45:588-589 (2013).
Jovaiša, T. et al., "Effects of ketamine on precipitated opiate withdrawal," Medicina (Kaunas), 42(8):625-634 (2006).
Kadriu, B. et al., "Acute ketamine administration corrects abnormal inflammatory bone markers in major depressive disorder," Molecular Psychiatry, 23:1626-1631 (2018).
Khanna, J. M. et al., "Effect of NMDA receptor antagonists on rapid tolerance to ethanol," European Journal of Pharmacology, 230:23-31 (1993).
Kolesnikov, Y. et al., "Blockade of Morphine-Induced Hindlimb Myoclonic Seizures in Mice by Ketamine," Pharmacology Biochemistry and Behavior, 56(3): 423-425 (1997).
Koob, G. F. "Neural Mechanisms of Drug Reinforcement," In P. W. Kalivas & H. H. Samson (Eds.), Annals of the New York Academy of Sciences: New York Academy of Sciences, 654:171-191 (1992).
Koob, G. F. & Volkow, N. D., "Neurobiological substrates for the dark side of compulsivity in addiction," Neuropharmacology, 56:18-31 (2009).
Koob, G. F., "Neurobiology of addiction: a neurocircuitry analysis," Lancet Psychiatry, 3:760-773 (2016).
Khorramzadeh, E. & Lofty, A. O., "The Use of Ketamine in Psychiatry," Psychosomatics, 14(6):344-346 (1973).

(56) References Cited

OTHER PUBLICATIONS

Koyuncuoğlu, H. et al., "Suppression by Ketamine and Dextromethorphan of Precipitated Abstinence Syndrome in Rats," Pharmacol Biochem Behav, 35(4):829-832 (1990).

Krystal, J. H. et al., "Subanesthetic Effects of the Noncompetitive NMDA Antagonist, Ketamine, in Humans," Arch Gen Psychiatry, 51:199-214 (1994).

Krystal, J. H. et al., "Rapid-Acting Glutamatergic Antidepressants: The Path to Ketamine and Beyond," Biol Psychiatry, 73:1133-1141 (2013).

Krupitsky, E. et al., "Anhedonia, depression, anxiety, and craving in opiate dependent patients stabilized on oral naltrexone or an extended release naltrexone implant," The American Journal of Drug and Alcohol Abuse, 42(5):614-620 (2016).

Langdon, K. J. et al., "Comorbidity of opioid-related and anxiety-related symptoms and disorders," Current Opinion in Psychology, 30:17-23 (2019).

Lapidus, K. A. et al., "A Randomized Controlled Trial of Intranasal Ketamine in Major Depressive Disorder," Biol Psychiatry, Published online Apr. 3, 2014, 17 pages; doi: 10.1016/j.biopsych.2014.03.026.

Li, F. et al., "Cannabinoid $CB_1$ receptor antagonist rimonabant attenuates reinstatement of ketamine conditioned place preference in rats," European Journal of Pharmacology, 589:122-126 (2008).

Li, S. X. et al., "Role of the NMDA receptor in cognitive deficits, anxiety and depressive-like behavior in juvenile and adult mice after neonatal dexamethasone exposure," Neurobiology of Disease, 62:124-134 (2014).

Liu, Y. et al., "Ketamine abuse potential anduse disorder," Brain Research Bulletin, 126:68-73 (2016).

Lopez, O. L. et al., "Risk Factors for Mild Cognitive Impairment in the Cardiovascular Health Study Cognition Study," Part 2, Arch Neurol., 60:1394-1399 (2003).

Ma, M. et al., "Key role of soluble epoxide hydrolase in the neurodevelopmental disorders of offspring after maternal immune activation," PNAS, 116(14):7083-7088 (2019).

Matsuura, A. et al., "Dietary glucoraphanin prevents the onset of psychosis in the adult offspring after maternal immune activation," Scientific Reports, 8:2158 (2018); doi:10.1038/s41598-018-20538-3,12 pages.

Millan, M. J. et al., "Cognitive dysfunction in psychiatric disorders: characteristics, causes and the quest for improved therapy," Nature Reviews Drug Discovery, 11:141-168 (2012).

Miller, N. S. et al., "The Relationship of Addiction, Tolerance, and Dependence to Alcohol and Drugs: A Neurochemical Approach," Journal of Substance Abuse Treatment, 4:197-207 (1987).

Mohammadi, A. et al., "Dysfunction in Brain-Derived Neurotrophic Factor Signaling Pathway and Susceptibility to Schizophrenia, Parkinson's and Alzheimer's Diseases," Current Gene Therapy, 18:45-63 (2018).

Muelken, P. et al., "A Two-Day Continuous Nicotine Infusion Is Sufficient to Demonstrate Nicotine Withdrawal in Rats as Measured Using Intracranial Self-Stimulation," PLoS One, 10(12):e0144553 (2015), 18 pages; doi:10.1371/journal.pone.0144553.

Napier, T. C. et al., "Using conditioned place preference to identify relapse prevention medications," Neuroscience and Biobehavioral Reviews, 37:2081-2086 (2013).

Negus, S. S. & Miller, L. L., "Intracranial Self-Stimulation to Evaluate Abuse Potential of Drugs," Pharmacol Rev 66:869-917 (2014).

Nikiforuk, A. & Popik, P., "The effects of acute and repeated administration of ketamine on attentional performance in the five-choice serial reaction time task in rats," Eur Neuropsychopharmacol., 24(8):1381-1393 (2014).

Pan, J. et al., "Blockade of the translocation and activation of c-Jun N-terminal kinase 3 (JNK3) attenuates dopaminergic neuronal damage in mouse model of Parkinson's disease," Neurochemistry International, 54:418-425 (2009).

Paslakis, G. et al., "Oral Administration of the NMDA Receptor Antagonist S-Ketamine as Add-On Therapy of Depression: A Case Series," Pharmacopsychiatry, 43:33-35 (2010).

Paul, R. et al., "Comparison of racemic ketamine and S-ketamine in treatment-resistant major depression: Report of two cases," The World Journal of Biological Psychiatry, 10(3):241-244 (2009).

Perry, M. B., "Perceptions of Mindfulness: A Qualitative Analysis of Group Work in Addiction Recovery," Rhode Island Medical Journal, 102:28-31 (2019).

Persson, J. et al., "The analgesic effect of racemic ketamine in patients with chronic ischemic pain due to lower extremity arteriosclerosis obliterans," Acta Anaesthesiol Scand, 42:750-758 (1998).

Persson, J. et al., "Pharmacokinetics and non-analgesic effects of S- and R-ketamines in health volunteers with normal and reduced metabolic capacity," Eur J Clin Pharmacol, 57:869-875 (2002).

Rodriguez, C. I. et al., "Randomized Controlled Crossover Trial of Ketamine in Obsessive-Compulsive Disorder: Proof-of-Concept," Neuropsychopharmacology, 38:2475-2483 (2013).

Pfenninger, E. G. et al., "Cognitive Impairment after Small-dose Ketamine Isomers in Comparison to Equianalgesic Racemic Ketamine in Human Volunteers," Anesthesiology, 96:357-366 (2002).

Rowland, L. M., "Subanesthetic Ketamine: How It Alters Physiology and Behavior in Humans," Aviat Space Environ Med, 76(7, Suppl.):C52-58 (2005).

Sams-Dodd, F., "Phencyclidine-induced stereotyped behaviour and social isolation in rats: a possible animal model of schhizophrenia," Behavioural Pharmacology, 7:3-23 (1996).

Schmidt, A. et al., "Cerebral physiological responses to bolus injection of racemic, S(+)- or R(-)-keamine in the pig," Acta Anaesthesiol Scand, 49:1436-1442 (2005).

Sekine, Y. et al., "Methamphetamine-Related Psychiatric Symptoms and Reduced Brain Dopamine Transporters Studied With PET," Am J Psychiatry, 158:1206-1214 (2001).

Shearman, G. T. et al., "Effectiveness of Lofexidine in Blocking Morphine-Withdrawal Signs in the Rat," Pharmacology Biochemistry & Behavior, 12:573-575 (1980).

Streel, E. et al., "Effects of anaesthetic agents in interference of naloxone-induced opiate-withdrawal are dose-dependent in opiate-dependent rats," Life Sciences, 77:650-655 (2005).

Suzuki, T. et al., "Effects of the non-competitive NMDA receptor antagonist ketamine on morphine-induced place preference in mice," Life Sciences, 67:383-389 (2000).

Tannock, I. F. et al., "Cognitive Impairment Associated With Chemotherapy for Cancer: Report of a Workshop," Journal of Clinical Oncology, 22(11):2233-2239 (2004).

Trujillo, K. A., "Effects of Noncompetitive N-Methyl-D-Aspartate Receptor Antagonists on Opiate Tolerance and Physical Dependence," Neuropsychopharmacology, 13:301-307(1995).

Tsai, S. -J., "TrkB partial agonists: Potential treatment strategy for epilepsy, mania, and autism," Medical Hypotheses, 66:173-175 (2006).

Tzschentke, T. M., "Measuring reward with the conditioned place preference (CPP) paradigm: update of the last decade," Addiction Biology, 12:227-462 (2007).

Van Dam, F. S. A. M., et al., "Impairment of Cognitive Function in Women Receiving Adjuvant Treatment for High-Risk Breast Cancer: High-Dose Versus Standard-Dose Chemotherapy," J. Natl Cancer Inst, 90(3):210-218 (1998).

Vayr, F. et al., "Barriers to seeking help for physicians with substance use disorder: A review," Drug and Alcholol Dependence, 199:116-121 (2019).

Vogels, R. L. C. et al., "Cognitive impairment in heart failure: A systematic review of the literature," European Journal of Heart Failure, 9:440-449 (2007).

Volkow, N. D. et al., "Association of Dopamine Transporter Reduction With Psychomotor Impairment in Methamphetamine Abusers," Am J Psychiatry, 158:377-382 (2001).

Volkow, N. D. et al., "Decreased striatal dopaminergic responsiveness in detoxified cocaine-dependent subjects," Nature, 386:830-833 (1997).

Vollenweider, F. X. et al., "Differential psychopathology and patterns of cerebral glucose utilization produced by (S)- and (R)-

(56) References Cited

OTHER PUBLICATIONS ketamine in healthy volunteers using positron emission tomography (PET)," Eur. Neuropsychopharmacol. 7:25-38 (1997).
Wang, C. et al., "Brain damages in ketamine addicts as revealed by magnetic resonance imaging," Front. Neuroanat., vol. 7, Article 23 (2013), 8 pages; doi.org/10.3389/fnana.2013.00023.
White, P. F. et al., "Comparative pharmacology of the ketamine isomers," Br. J. Anaesth., 57:197-203 (1985).
Wink, L. K. et al., "Intranasal Ketamine Treatment in an Adult With Autism Spectrum Disorder," J Clin Psychiatry, 75(8):835-836 (2014).
Womble, A. L., "Effects of Ketamine on Major Depressive Disorder in a Patient with Posttraumatic Stress Disorder," AANA Journal, 81(2):118-119 (2013).
Xiaoyin, K. et al., "The profile of cognitive impairments in chronic ketamine users," Psychiatry Research, 266:124-131 (2018).
Yamamoto, N. et al., "Ketamine reduces amyloid -protein degradation by suppressing neprilysin expression in primary cultured astrocytes," Neuroscience Letters, 545:54-58 (2013).
Yang, C. et al., "R-ketamine: a rapid-onset and sustained antidepressant without psychotomimetic side effects," Transl Psychiatry, 5:e632 (2015), 11 pages; doi:10.1038/tp.2015.136.
Yang, C. et al., "Loss of parvalbumin-immunoreactivity in mouse brain regions after repeated intermittent administration of esketamine, but not R-ketamine," Psychiatry Research, 239:281-283 (2016).
Yoon, G. et al., "Association of Combined Naltrexone and Ketamine With Depressive Symptoms in a Case Series of Patients With Depression and Alcohol Use Disorder," JAMA Psychiatry, published online Jan. 9, 2019; doi:10.1001/jamapsychiatry.2018.3990, 2 pages.
Zanos, P. et al., "NMDAR inhibition-independent antidepressant actions of ketamine metabolites," Nature, 533:481-486 (2016), and Methods, 12 pages.
Zarate, C. A. et al., "A Randomized Trial of an N-methyl-d-aspartate Antagonist in Treatment-Resistant Major Depression," Arch Gen Psychiatry, 63: 856-864 (2006).
Zhang, J. -c, Z. et al., "$R(-)$-ketamine shows greater potency and longer lasting antidepressant effects than $S(+)$-ketamine," Pharmacology, Biochemistry and Behavior, 116:137-141 (2014).
Zhang, K. et al., "Role of Inflammatory Bone Markers in the Antidepressant Actions of (R)-Ketamine in a Chronic Social Defeat Stress Model," International Journal of Neuropsychopharmacology, 21(11):1025-1030 (2018).
Ago, Y. et al., "(R)-ketamine induces a greater increase in prefrontal 5-HT release than (S)-ketamine and ketamine metabolites via an AMPA receptor-independent mechanism," Int J Neuropsychopharmacol, 22(10):665-674 (2019).
CDC. National Violent Death Reporting System. 2015; 2 pages; Available from: www.cdc.gov/violenceprevention/nvdrs/index.html.
Canuso, C.M. et al., "Efficacy and safety of intranasal esketamine for the rapid reduction of symptoms of depression and suicidality in patients at imminent risk for suicide: results of a double-blind, randomized, placebo-controlled study," Am J Psychiatry, 175(7):620-630 (2018).
Chan, W. -H. et al., "Induction of rat hepatic cytochrome P-450 by ketamine and its toxicological implications", J Toxicol Environ Health A, 68(17-18):1581-1597 (2005).
Chang, L. et al., "Comparison of antidepressant and side effects in mice after intranasal administration of (R,S)-ketamine, (R)-ketamine, and (S)-ketamine," Pharmacol Biochem Behav, 181:53-59 (2019).
Chang, L. et al., "Lack of dopamine D1 receptors in the antidepressant actions of (R)-ketamine in a chronic social defeat stress model," Eur Arch Psychiatry Clin Neurosci, 270:271-275 (2020).
Ezquerra-Romano, I. I. et al., "Ketamine for the treatment of addiction: Evidence and potential mechanisms," Neuropharmacology, 142:72-82 (2018).
Ide, S. et al. "Cognitive impairment that is induced by (R)-ketamine is abolished in NMDA GluN2D receptor subunit knockout mice," Int J Neuropsychopharmacol, 22(7):449-452 (2019).

Ivanova, J. I. et al., "Direct and indirect costs of employees with treatment-resistant and non-treatment-resistant major depressive disorder," Curr Med Res Opin, 26(10):2475-2484 (2010).
Janssen Pharmaceutical Companies. Medication Guide Spravato™ CIII (esketamine) nasal spray: prescribing information. 2020. Titusville, NJ, USA, 44 pages.
Klepstad, P. et al., "Evidence of a role for NMDA receptors in pain perception," Eur J Pharmacol, 187(3):513-518 (1990).
Leal, G. C. et al., "Intravenous arketamine for treatment-resistant depression: open-label pilot study," Eu Arch Psych Clin Neurosci, 271:577-582 (2021).
Li, J. -M. et al., "Ketamine may exert antidepressant effects via suppressing NLRP3 inflammasome to upregulate AMPA receptors," Neuropharmacology, 146:149-153 (2019).
Mathisen, L.C. et al., "Effect of ketamine, an NMDA receptor inhibitor, in acute and chronic orofacial pain," Pain, 61(2):215-220 (1995).
Mizukami,K., "Alzheimer's Disease and Depression," Journal of Neurology, 115(11):1122-1125 (2013). English Abstract Only.
Mudter, J. & Neurath, M. F., "IL-6 Signaling in Inflammatory Bowel Disease: Pathophysiological Role and Clinical Relevance," Inflamm Bowl Dis., 13(8):1016-1023 (2007).
Oye, I. et al., "Effects of ketamine on sensory perception: evidence for a role of N-methyl-D-aspartate receptors," J Pharmacol Exp Ther, 260(3):1209-1213 (1992).
Pfenninger, E. G. et al., "Cognitive impairment after small-dose ketamine isomers in comparison to equianalgesic racemic ketamine in human volunteers," Anesthesiology, 96(2):357-366 (2002).
Shah, S. et al., "Combination of oral ketamine and midazolam as a premedication for a severely autistic and combative patient," J Anesth, 23:126-128 (2009).
Sheehan, D. V. et al., "The Mini-International Neuropsychiatric Interview (M.I.N.I.): the development and validation of a structured diagnostic psychiatric interview for DSM-IV and ICD-10," J Clin Psychiatry, 59 Suppl 20:22-33 (1998).
Shirayama, Y. & Hashimoto, K., "Effects of a single bilateral infusion of R-ketamine in the rat brain regions of a learned helplessness model of depression," Eur Arch Psychiatry Clin Neurosci, 267(2):177-182 (2017).
Shirayama & Hashimoto, "Lack of antidepressant effects of (2R,6R)-hydroxynorketamine in a rat learned helplessness model: comparison with (R)-ketamine," Int J Neuropsychopharmacol, 21(1):84-88 (2018).
Souery, D. et al., "Clinical factors associated with treatment resistance in major depressive disorder: results from a European multicenter study," J Clin Psychiatry, 68(7):1062-1070 (2007).
Tian, Z. et al., "Expression of heat shock protein HSP-70 in the retrosplenial cortex of rat brain after administration of (R,S)-ketamine and (S)-ketamine, but not (R)-ketamine," Pharmacol Biochem Behav, 172:17-21 (2019).
WHO. Depression. 2017; 5 pages; Available from: www.who.int/news-room/factsheets/detail/depression.
Yang, C. et al., "(R)-ketamine shows greater potency and longer lasting antidepressant effects than its metabolite (2R,6R)-hydroxynorketamine," Biol Psychiatry, 82(5):e43-e44 (2017), 2 pages.
Yang, C. et al., "Possible role of the gut microbiota-brain axis in the antidepressant effects of (R)-ketamine in a social defeat stress model," Transl Psychiatry, 7(12):1294 (2017), 11 pages.
Yang, C. et al., "AMPA Receptor Activation-Independent Antidepressant Actions of Ketamine Metabolite (S)-Norketamine," Biol Psychiatry, 84(8):591-600 (2018).
Zanos, P. et al., "(R)-ketamine exerts antidepressant actions partly via conversion to (2R,6R)-hydroxynorketamine, while causing adverse effects at sub-anesthetic doses," Br J Pharmacol, 176(14):2573-2592 (2019).
Zanos, P. & Gould, T. D., "Intracellular signaling pathways involved in (S)- and (R)-ketamine antidepressant actions," Biol Psychiatry, 83(1):2-4 (2018).
Zanos, P. et al., "Ketamine and ketamine metabolite pharmacology: insights into therapeutic mechanisms," Pharmacol Rev, 70(3):621-660 (2018).

(56) References Cited

OTHER PUBLICATIONS

Zhang, M. et al., "Effects of subanesthetic intravenous ketamine infusion on neuroplasticity-related proteins in the prefrontal cortex, amygdala, and hippocampus of Sprague-Dawley rats," IBRO Rep, 6:87-94 (2019).
Coiro, P. et al., "Impaired synaptic development in a maternal immune activation mouse model of neurodevelopmental disorders," Brain, Behavior, and Immunity, 50:249-258 (2015).
Solanki, I. et al., "Neurodegenerative diseases: From available treatments to prospective herbal therapy," Neurochemistry International, 95:100-108 (2016). 17 pages provided.
Zhu, W. et al., "Risks Associated with Misuse of Ketamine as a Rapid-Acting Antidepressant," Neurosci. Bull., 32(6):557-564 (2016).
Ruda-Kucerova, J. et al., "Both ketamine and NBQX attenuate alcohol drinking in male Wistar rats," Neuroscience Letters, 2018, 666:175-180.
Mion, G. & Villevieille, T., "Ketamine pharmacology: an update (pharmacodynamics and molecular aspects, recent findings)," CNS Neurosci Ther., 19(6):370-80 (2013); doi: 10.1111/cns.12099. Epub Apr. 10, 2013.
Bremner, J. D. et al., "Measurement of Dissociative States with the Clinician-Administered Dissociative States Scale (CADSS)," Journal of Traumatic Stress, 11(1):125-136 (1998).
Daly, E. J. et al., "Efficacy and Safety of Intranasal Esketamine Adjunctive to Oral Antidepressant Therapy in Treatment-Resistant Depression A Randomized Clinical Trial," JAMA Psychiatry, 2018; 75(2): 139-148. doi: 10.1001/jamapsychiatry.2017.3739; Published online Dec. 27, 2017.
Enarson, M. C. et al., "Clinical Experience with Oral Ketamine," Journal of Pain and Symptom Management, 17(5):384-386 (1999).
Fava, M. et al., "Double-blind, placebo-controlled, dose-ranging trial of intravenous ketamine as adjunctive therapy in treatment-resistant depression (TRD)," Molecular Psychiatry (2020) 25:1592-1603, https://doi.org/10.1038/s41380-018-0256-5.
Galvez, V. et al., "Long-Lasting Effects of a Single Subcutaneous Dose of Ketamine for Treating Melancholic Depression: A Case Report," Biol. Psychiatry, 2014; 76 e1-e2, 2 pages.
George, D. et al., "Pilot Randomized Controlled Trial of Titrated Subcutaneous Ketamine in Older Patients with Treatment-Resistant Depression," Am J Geriatr Psychiatry 2017; 25:1199-1209.
Glue, P. et al., "Safety and efficacy of maintenance ketamine treatment in patients with treatment-refractory generalised anxiety and social anxiety disorders," Journal of Psychopharmacology 2018, vol. 32(6) 663-667.
Hasler, F. et al. Acute psychological and physiological effects of psilocybin in healthy humans: A double-blind, placebo-controlled dose-effect study. Psychopharmacology (2004); 172(2):145-156.
Kavalali, E. T. & Monteggia, L. M., "Synaptic Mechanisms Underlying Rapid Antidepressant Action of Ketamine," Am J Psychiatry 2012; 169:1150-1156.
Kroenke, K. et al., "The PHQ-9 Validity of a Brief Depressive Severity Measure," J Gen Intern Med, 16:606-613 (2001).
Loo, C. K. et al., "Placebo-controlled pilot trial testing dose titration and intravenous, intramuscular and subcutaneous routes for ketamine in depression," Acta Psychiatr Scand 2016: 134: 48-56.
Murrough, J. W. et al., "Rapid and Longer-Term Antidepressant Effects of Repeated Ketamine Infusions in Treatment-Resistant Major Depression," Biol Psychiatry 2013;74:250-256; dx.doi.org/10.1016/j.biopsych.2012.06.022.
Overall, J. E. & Gorham, D. R., "The Brief Psychiatric Rating Scale," Psychological Reports, 10:799-812 (1962).
Pambianco, D. J. et al., "Computer-assisted personalized sedation for upper endoscopy and colonoscopy: a comparative, multicenter randomized study," Gastrointest Endosc 2011;73:765-72.
Reich, D. L. & Silvay, G., "Ketamine: an update on the first twenty-five years of clinical experience," Can J Anaesth, 1989, 36(2): 186-197.

Reus G.Z., et al., "A Single Dose of S-Ketamine Induces Long-Term Antidepressant Effects and Decreases Oxidative Stress in Adulthood Rats Following Maternal Deprivation," Developmental Neurobiology, Nov. 2015, vol. 75(11), pp. 1268-1281.
Rugani, F. et al., "Symptomatological Features of Patients with and without Ecstasy Use during Their First Psychotic Episode," Int. J. Environ. Res. Public Health 2012, 9: 2283-2292; doi:10.3390/ijerph9072283.
Sanacora, G., "New Understanding of Mechanisms of Action of Bipolar Medications," J Clin Psychiatry 2008; 69 (suppl 5): 22-27, 6 pages.
Schmid, R. L. et al., "Use and efficacy of low-dose ketamine in the management of acute postoperative pain: a review of current techniques and outcomes," Pain, 82:111- 125 (1999).
Singh, J. B. et al., "A Double-Blind, Randomized, Placebo-Controlled, Dose-Frequency Study of Intravenous Ketamine in Patients With Treatment-Resistant Depression," AmJ Psychiatry 2016; 173:816-826; doi: 10.1176/appi.ajp.2016.16010037.
Singh, J. B. et al., "Intravenous Esketamine in Adult Treatment-Resistant Depression: A Double-Blind, Double-Randomization, Placebo-Controlled Study," Biological Psychiatry, 80(6):424-431 (2016).
Singh, V. et al., "Intranasal Ketamine and Its Potential Role in Cancer-Related Pain," Pharmacotherapy 2018; 38(3):390-401; doi: 10.1002/phar.2090.
Spitzer, R. L. et al., "Validation and Utility of a Self-report Version of PRIME-MD. The PHQ Primary Care Study," Nov. 1999, JAMA The Journal of the American Medical Association 282(18):1737-1744.
Spitzer, R. L. et al., "Validity and utility of the PRIME-MD Patient Health Questionnaire in assessment of 3000 obstetric-gynecologic patients: The PRIME-MD Patient Health Questionnaire Obstetrics-Gynecology Study," Am J Obstet Gynecol 2000;183:759-769.
Studerus, E et al. (2010) Psychometric evaluation of the altered states of consciousness rating scale (OAV). PloS One, 5:e12412, 19 pages.
Tamoaka et al., "Differential Diagnosis and Current Treatment of Dementia" Divine Healing, 2016. Vol. 33 No. 2 pp. 125-130.
Vollenweider, F. X. et al., "Metabolic hyperfrontality and psychopathology in the ketamine model of psychosis using positron emission tomography (PET) and [18F]fluorodeoxyglucose (FDG)," European Neuropsychopharmacology 7 (1997) 9-24.
Zarate, C. A. et al., "Replication of Ketamine's Antidepressant Efficacy in Bipolar Depression: A Randomized Controlled Add-On Trial," Biol Psychiatry 2012;71:939- 946; doi:10.1016/j.biopsych.2011.12.010.
Zhuo, C. et al., "Effects of ketamine on circadian rhythm and synaptic homeostasis in patients with treatment-resistant depression: A protocol for mechanistic studies of its rapid and sustained antidepressant actions in humans," Brain and Behavior, 2019; 9:e01423, 11 pages; doi.org/10.1002/brb3.1423.
Gammaitoni, A. et al., "Topical Ketamine Gel: Possible Role in Treating Neuropathic Pain," Pain Medicine, 1(1):97-100 (2000).
Krupitsky, E. et al., "Ketamine Psychotherapy for Heroin Addiction: Immediate Effects and Two-year Follow-up", Journal of Substance Abuse Treatment, vol. 23, No. 4, pp. 273-283, 2002.
Krupitsky, E. M. et al., "Ketamine psychedelic therapy (KPT): A review of the results of ten years of research", Journal of Psychoactive Drugs, vol. 29, No. 2, Jan. 1, 1997, pp. 165-183.
Wang, S. & Li, C., "Synthesis of anesthetic compound 2-(o-fluorophenyl)-2-methylaminocyclohexanone hydrochloride (F-ketamine)," Beijing Daxue Xuebao, Ziran Kexueban, 1987, Issue 2, pp. 116-119, with English Abstract, 4 pages.
Wang, S. & Li, C., "Synthesis of anesthetic compound 2-(o-fluorophenyl)-2-methylaminocyclohexanone hydrochloride (F-ketamine)," Beijing Daxue Xuebao, Ziran Kexueban, 1987, Issue 2, Abstract, 1 page.

\* cited by examiner

[FIG. 2]
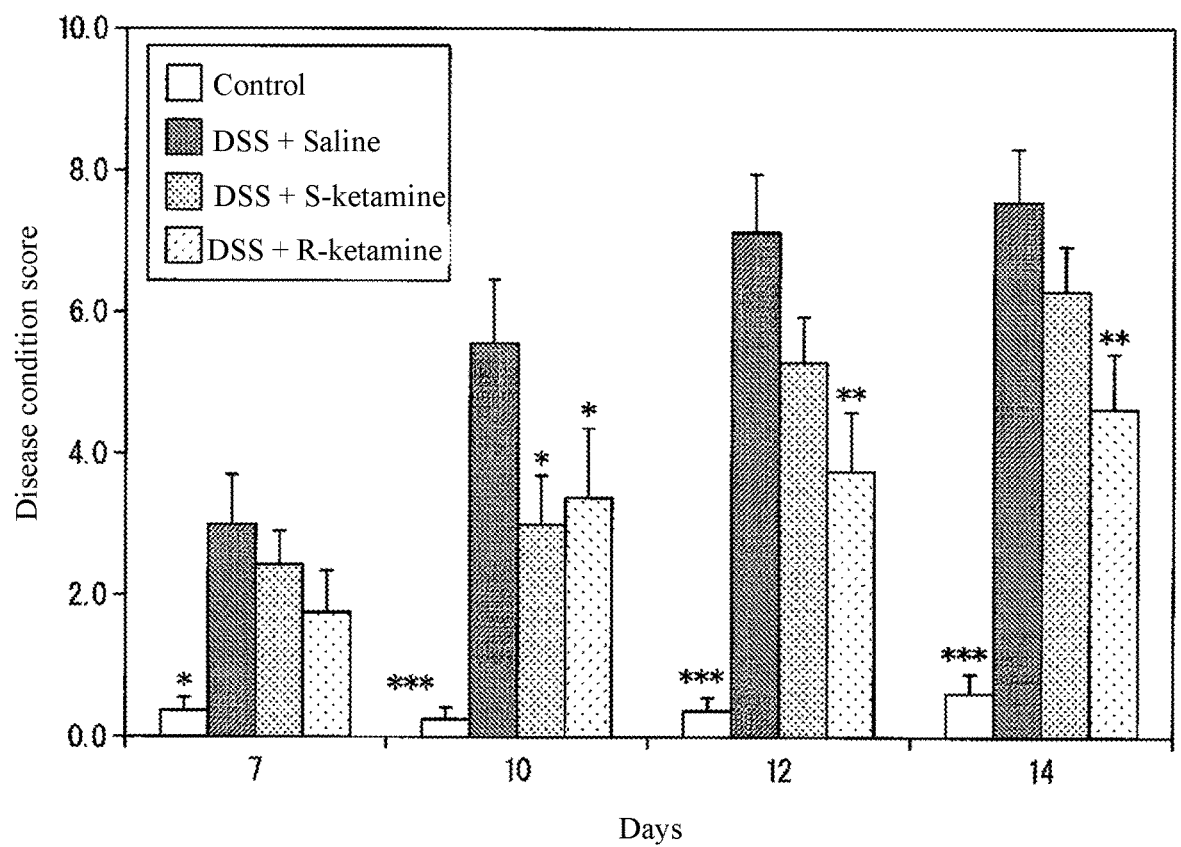

[FIG. 3]
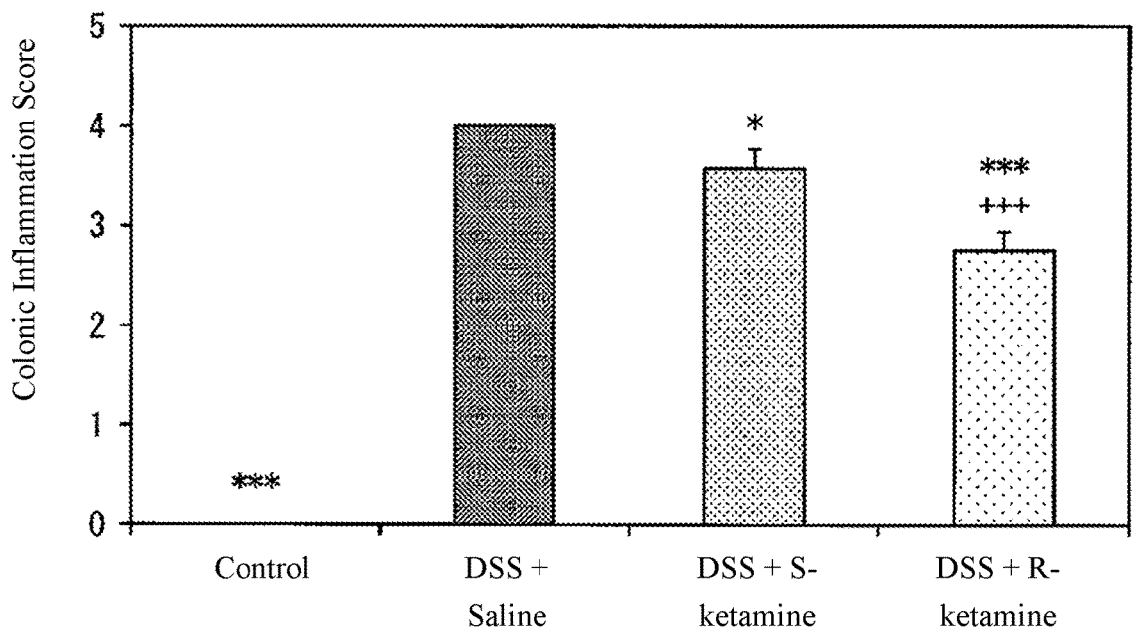
[FIG. 4]
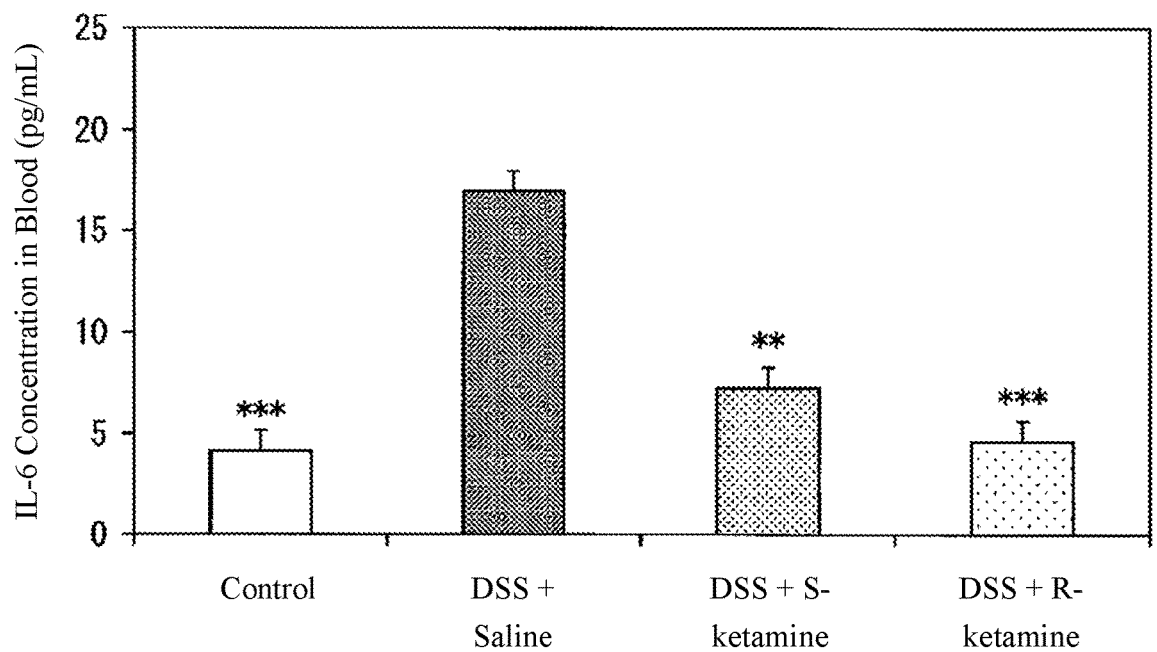

[FIG. 8]

PREVENTIVE OR THERAPEUTIC AGENT AND PHARMACEUTICAL COMPOSITION FOR INFLAMMATORY DISEASES OR BONE DISEASES

CROSS REFERENCE TO RELATED APPLICATIONS

This application is a U.S. National Phase Application, filed under 35 USC § 371, of International Patent Application No. PCT/JP2019/005415, filed Feb. 14, 2019, which claims priority to JP 2018-025170 filed in Japan on Feb. 15, 2018, and JP 2018-121858 filed in Japan on Jun. 27, 2018, the contents of each of which are incorporated by reference herein in their entirety.

TECHNICAL FIELD

The present invention relates to a preventative or therapeutic agent for an inflammatory disease or a bone disease, and a pharmaceutical composition for preventing or treating an inflammatory disease or a bone disease.

BACKGROUND ART

Inflammation is a major cause of many chronic inflammatory diseases. Furthermore, long-term inflammation leads to tissue destruction and causes extensive damage and the eventual dysfunction of inflamed organs.

Chronic inflammatory diseases are involved in defined tissues or organs. For example, chronic inflammatory diseases in musculoskeletal tissue are a cause of diseases such as rheumatoid arthritis and ankylosing spondylitis. Furthermore, chronic inflammatory diseases in the digestive tract are a cause of diseases such as Crohn's disease and ulcerative colitis. Moreover, chronic inflammatory diseases in pancreatic β cells are a cause of diseases such as insulin-dependent diabetes. Furthermore, chronic inflammatory diseases in the adrenal glands are a cause of diseases such as Addison's disease. Moreover, chronic inflammatory diseases in the kidneys are a cause of diseases such as Goodpasture syndrome, IgA nephropathy, and interstitial nephritis. Furthermore, chronic inflammatory diseases in the exocrine glands are a cause of diseases such as Sjögren's syndrome and autoimmune pancreatitis. Moreover, chronic inflammatory diseases of the skin are a cause of diseases such as psoriasis and atopic dermatitis. Furthermore, chronic inflammatory diseases in the respiratory tract are a cause of diseases such as pneumonia, chronic bronchitis, and bronchial asthma. Moreover, chronic inflammatory diseases are also known to be involved in multiple organs, such as systemic lupus erythematosus (SLE) and scleroderma.

These chronic inflammatory diseases are increasing worldwide. Furthermore, it is a fact that current treatments do not provide sufficient treatment.

Among chronic inflammatory diseases, the general term for diseases of unknown cause that induce chronic inflammation or ulceration of mucous membranes of the large and small intestines is inflammatory bowel disease (inflammatory bowel disease: IBD). Inflammatory bowel disease is mainly classified into ulcerative colitis and Crohn's disease, and both are designated as defined diseases (orphan diseases). Characteristic symptoms include bloody stool, mucous stool, diarrhea, abdominal pain, and the like, and these symptoms are further characterized as repeatedly improving (remission) and worsening (deterioration).

The number of patients having ulcerative colitis in Japan was over 160,000 at the end of 2013, which is about 100 people per 100,000 population. Furthermore, the number of patients having Crohn's disease was less than 40,000 at the end of 2013, which is around 27 people per 100,000 population.

Along with the westernization of dietary habits, both ulcerative colitis and Crohn's disease are on course to increase every year. Furthermore, the number of patients per unit population in the United States and Europe is said to be around several to ten times that of Japan, thereby constituting a major social problem.

As it is difficult to completely cure inflammatory bowel disease, the main goal of current treatments is to lead to remission and extend the time to surgical treatment by maintaining long-term remission. Basically, pharmacotherapy or cytapheresis therapy is performed, and surgical treatment is performed as necessary.

For example, although steroids often used in pharmacotherapy have strong anti-inflammatory effects, they have significant side effects, so it is desirable to avoid taking them for a long period of time; thus, they are not suitable for the purpose of maintaining remission of inflammatory bowel disease.

Furthermore, the result of long-term administration of steroids may also lead to refractory colitis that is steroid-resistant, steroid-dependent, or the like. Moreover, in severe cases and refractory cases, a large amount of steroids is administered from the beginning of treatment, so there is a problem in that many side effects appear.

Azathioprine and 6-mercaptopurine (6-MP), which are immunomodulators, are used as substitutes for the purpose of reducing the amount of steroids used; however, it takes about two to three months for the effects of these drugs to be expressed.

Furthermore, in pharmacotherapy for inflammatory bowel disease, a biopharmaceutical such as an anti-TNFα antibody (infliximab, adalimumab, or the like) may be used. However, infliximab has been reported to have side effects due to immunosuppression, including infections, such as Mycobacterium tuberculosis infection, sepsis, or pneumonia, and liver damage, rash, or leukopenia. Moreover, it has also been reported that antibodies against these antibody preparations are produced and thus the effect is diminished.

Furthermore, an anti-TNFα antibody preparation is usually used in combination with immunomodulators (azathioprine and 6-MP) to maintain the effect thereof; however, a problem has been identified in that these combinations increase carcinogenic risk.

Moreover, 5-aminosalicylic acid drugs are widely used for mild to moderate ulcerative colitis and Crohn's disease, but they tend to be less effective for severe patients.

Incidentally, ketamine is a compound known as an allylcyclohexylamine-based dissociative anesthetic, and is a racemic compound which is a mixture of equal amounts of R-ketamine and S-ketamine. Ketamine is known as an NMDA receptor antagonist. Ketamine has a significant advantage in that it does not inhibit respiration at low doses as compared to other common anesthetics, and it is often used as an anesthetic in animals.

For example, Non Patent Literature 1 reports that ketamine has an anti-inflammatory effect in ulcerative colitis model mice.

Incidentally, bone homeostasis is maintained by remodeling (bone remodeling), wherein osteoclasts destroy and resorb old bones, and osteoblasts form new bones. If the balance of this bone remodeling is lost for various reasons and bone destruction and resorption becomes superior to bone formation, bone diseases such as osteoporosis, osteolytic bone metastasis, and Paget's disease of the bone are induced.

Along with the recent advent of a super-aging society, the number of patients having bone diseases such as osteoporosis is increasing, and it is estimated that there are about 13 million patients in Japan. For example, although it is known that osteoporosis can be caused by various factors such as lack of calcium and magnesium, which form bone, lack of a balanced intake of vitamins such as vitamin D, which is necessary for calcium absorption, lack of exercise, aging, and menopause, its pathogenic mechanism is still unknown.

Furthermore, rheumatoid arthritis, which is caused by inflammation due to an immune abnormality or the like, is characterized by chronic polysynovitis with a background of systemic autoimmunity, and accompanying bone destruction. There is a tendency for rheumatoid arthritis to increase year by year, and an important challenge is to investigate the causes of bone loss and bone destruction in these patients and to develop treatments.

Receptor activator of nuclear factor κB ligand (RANKL) produced from osteoblasts promotes osteoclast formation, function, and the like. Therefore, excessive production of RANKL for any reason leads to excessive bone resorption.

Although infiltration of activated T cells and B cells, abnormal proliferation of synovial fibroblasts, and the like occurs in the joints of patients having rheumatoid arthritis, RANKL is highly expressed in these cells, so it is thought that facilitation of the formation, function, and survival of osteoclasts induces bone destruction near joints.

Denosumab, a therapeutic agent for bone diseases, is a human monoclonal antibody preparation targeting RANKL. This preparation exhibits an effect of improving bone disease by binding to RANKL and inhibiting the function of RANKL, thereby suppressing facilitation of bone resorption by osteoclasts and increasing bone density. Furthermore, an effect is exhibited wherein by inhibiting the function of RANKL, it suppresses bone resorption by osteoclasts at joint areas and suppresses the progression of bone erosion and bone destruction at joints in rheumatoid arthritis patients (for example, see Patent Literature 1).

PRIOR ART LITERATURE

Patent Literature

Patent Literature 1: Japanese Patent No. 4401613

Non Patent Literature

Non Patent Literature 1: Ashry E. E., et al., Protective Effect of Ketamine Against Acetic Acid-Induced Ulcerative Colitis in Rats, Pharmacology & Pharmacy, 7, 9-18, 2016.

SUMMARY OF INVENTION

Problem to be Solved by Invention

However, ketamine is used at a high dose of 50 mg/kg in Non Patent Document 1, which describes that ketamine has an anti-inflammatory effect. This kind of dose is an anesthetic dose, and a side effect such as an acute momentum facilitation effect is markedly observed. It is impractical to administer an anesthetic dose of ketamine to a patient for the purpose of preventing or treating an inflammatory disease.

Furthermore, denosumab is not a fundamental therapeutic agent for bone diseases. Moreover, it is known that when denosumab is administered to a patient having a bone disease, severe side effects may occur, such as hypocalcemia, osteonecrosis of the jaw, osteomyelitis of the jaw, anaphylaxis, atypical fractures such as trochanteric femoral fractures and proximal femoral shaft fractures, and skin infections.

Against this background, the object of the present invention is to provide a preventive or therapeutic agent and a pharmaceutical composition for an inflammatory disease or a bone disease.

Means for Solving Problem

The present invention includes the following aspects.

[1] A preventative or therapeutic agent for an inflammatory disease or a bone disease, containing as an active ingredient a compound represented by the following formula (1) or a pharmacologically acceptable salt thereof.

[Formula 1]

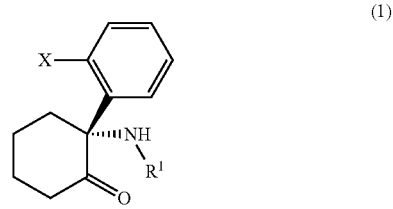

(1)

[In formula (1), X represents a hydrogen atom, a halogen atom, or a $C_1$-$C_{10}$ alkyl group that may be substituted; $R^1$ represents a $C_1$-$C_{10}$ alkyl group that may be substituted, a $C_1$-$C_{10}$ alkenyl group that may be substituted, or a $C_6$-$C_{14}$ aryl group that may be substituted; and one or more hydrogen atoms may be substituted for deuterium atoms.]

[2] The preventative or therapeutic agent for an inflammatory disease or a bone disease according to [1], wherein the preventative or therapeutic agent contains as an active ingredient a compound represented by the following formula (2) or a pharmacologically acceptable salt thereof.

[Formula 2]

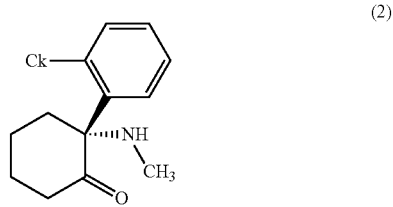

(2)

[In formula (2), one or more hydrogen atoms may be substituted for deuterium atoms.]

[3] The preventative or therapeutic agent for an inflammatory disease or a bone disease according to [1] or [2], wherein the inflammatory disease is ulcerative colitis, Crohn's disease, rheumatoid arthritis, ankylosing spondylitis, insulin-dependent diabetes, Addison's disease, Goodpasture syndrome, IgA nephropathy, interstitial nephritis, Sjögren's syndrome, autoimmune pancreatitis, psoriasis, atopic dermatitis, pneumonia, chronic bronchitis, bronchial asthma, systemic lupus erythematosus (SLE), scleroderma, or delirium, and the bone disease is osteoporosis, osteolytic bone metastasis, or Paget's disease of bone.

[4] The preventative or therapeutic agent for an inflammatory disease or a bone disease according to any of [1] to [3], wherein the preventative or therapeutic agent does not substantially contain a compound represented by the following formula (3) or a pharmacologically acceptable salt thereof.

[Formula 3]

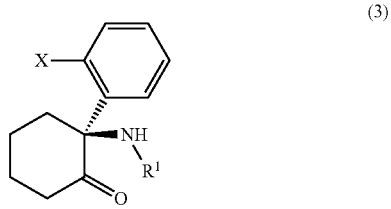

(3)

[In formula (3), X represents a hydrogen atom, a halogen atom, or a $C_1$-$C_{10}$ alkyl group that may be substituted; and $R^1$ represents a $C_1$-$C_{10}$ alkyl group that may be substituted, a $C_1$-$C_{10}$ alkenyl group that may be substituted, or a $C_6$-$C_{14}$ aryl group that may be substituted.]

[5] A preventative or therapeutic agent for an inflammatory disease or a bone disease according to [4], wherein the preventative or therapeutic agent does not substantially contain a compound represented by the following formula (4) or a pharmacologically acceptable salt thereof.

[Formula 4]

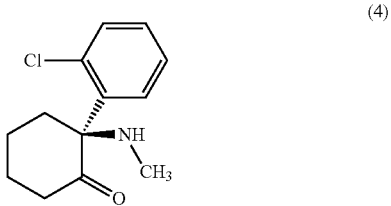

(4)

[6] A pharmaceutical composition for preventing or treating an inflammatory disease or a bone disease, wherein the pharmaceutical composition contains the preventative or therapeutic agent for an inflammatory disease or a bone disease according to any of [1] to [5], and a pharmacologically acceptable carrier.

Effect of Invention

According to the present invention, it is possible to provide a preventative or therapeutic agent and pharmaceutical composition for an inflammatory disease or a bone disease.

BRIEF DESCRIPTION OF DRAWINGS

FIG. 2 A graph showing the results of Experimental Example 2.

FIG. 3 A graph showing the results of Experimental Example 3.

FIG. 4 A graph showing the results of Experimental Example 4.

MODE FOR CARRYING OUT THE INVENTION

Figure 1:
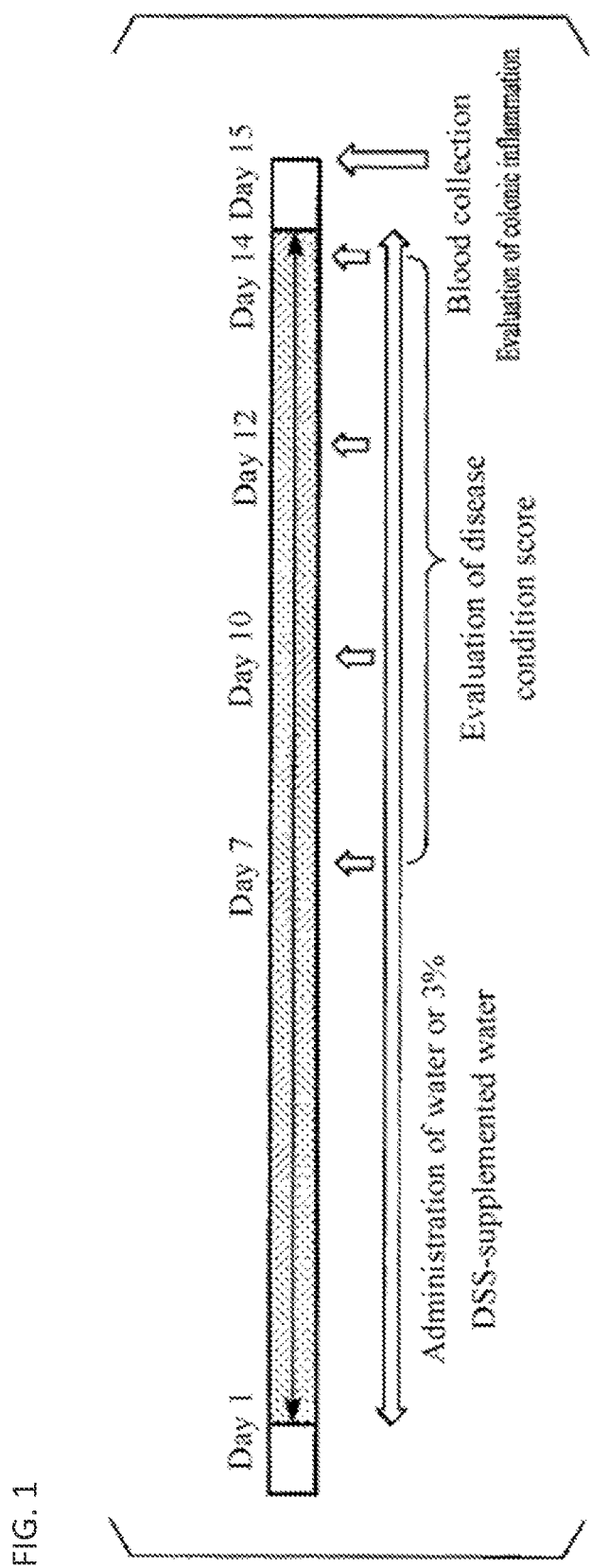
FIG. 1 A schematic diagram describing the experimental schedule of Experimental Example 1.

Preventative or Therapeutic Agent for Inflammatory Disease

In one embodiment, the present invention provides a preventative or therapeutic agent for an inflammatory disease or a bone disease, containing as an active ingredient a compound represented by the following formula (1) or a pharmacologically acceptable salt thereof. The preventive or therapeutic agent for a bone disease will be described later. As will be described later in examples, it is possible to prevent or treat an inflammatory disease with the preventative or therapeutic agent of the present embodiment.

[Formula 5]

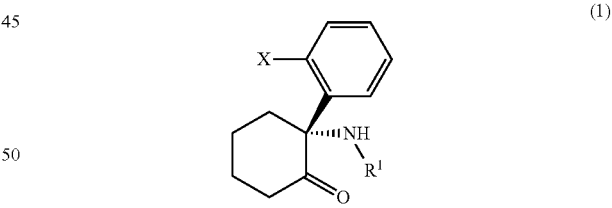

(1)

[In formula (1), X represents a hydrogen atom, a halogen atom, or a $C_1$-$C_{10}$ alkyl group that may be substituted; $R^1$ represents a $C_1$-$C_{10}$ alkyl group that may be substituted, a $C_1$-$C_{10}$ alkenyl group that may be substituted, or a $C_6$-$C_{14}$ aryl group that may be substituted; and one or more hydrogen atoms may be substituted for deuterium atoms.]

In the present specification, "containing as an active ingredient" means that which is included as the main active substance, and the content thereof is not particularly limited, provided that it includes as a medicinal ingredient the compound represented by the foregoing formula (1) or a pharmacologically acceptable salt thereof.

In the preventative or therapeutic agent for an inflammatory disease of the present embodiment, inflammatory bowel diseases such as ulcerative colitis or Crohn's disease, rheumatoid arthritis, ankylosing spondylitis, insulin-dependent diabetes, Addison's disease, Goodpasture syndrome, IgA nephropathy, interstitial nephritis, Sjögren's syndrome, autoimmune pancreatitis, psoriasis, atopic dermatitis, pneumonia, chronic bronchitis, bronchial asthma, systemic lupus erythematosus (SLE), scleroderma, or delirium may be listed as examples of the "inflammatory disease." The preventative or therapeutic agent of the present embodiment is especially effective against inflammatory bowel diseases such as ulcerative colitis and Crohn's disease, and as will be described later in examples, it is particularly effective against ulcerative colitis.

Since inflammatory diseases are chronic diseases that progress over a long period of time (years), beginning treatment early may prevent the progression of symptoms. Furthermore, by administering an agent to patients having a genetic background that is potentially susceptible to inflammatory diseases before they exhibit symptoms of an inflammatory disease, it may also be used to prevent the onset of an inflammatory disease.

It may be stated that the preventative or therapeutic agent of the present embodiment is an agent for preventing the onset of an inflammatory disease, and also that it is an agent for preventing the progression of inflammatory disease symptoms. Furthermore, it may be stated that the preventative or therapeutic agent of the present embodiment is a therapeutic agent for preventing the progression of inflammatory disease symptoms and alleviating or improving symptoms.

In the compound represented by the foregoing formula (1), X represents a hydrogen atom, a halogen atom, or a $C_1$-$C_{10}$ alkyl group that may be substituted. F, Cl, Br, or I may be listed as examples of the halogen atom. A methyl group, ethyl group, propyl group, isopropyl group, cyclopropyl group, butyl group, isobutyl group, t-butyl group, cyclobutyl group, cyclopropylmethyl group, pentyl group, cyclopentyl group, or the like may be listed as examples of the $C_1$-$C_{10}$ alkyl group. Furthermore, for example, a halogen atom such as F, Cl, Br, or I, a hydroxyl group, or the like may be listed as examples of a substituent of the alkyl group.

Furthermore, in the compound represented by the foregoing formula (1), $R^1$ represents a $C_1$-$C_{10}$ alkyl group that may be substituted, a $C_1$-$C_{10}$ alkenyl group that may be substituted, or a $C_6$-$C_{14}$ aryl group that may be substituted.

When $R^1$ is an alkyl group, the number of carbon atoms of the alkyl group is 1 to 10, and preferably 1 to 6. The alkyl group may be linear, may be branched, and may form a ring.

For example, a halogen atom such as F, Cl, Br, or I, a hydroxyl group, or the like may be listed as examples of a substituent of the alkyl group.

The $C_1$-$C_{10}$ alkyl group is not particularly limited as long as the effects of the present embodiment are exhibited, and, for example, a methyl group, ethyl group, propyl group, isopropyl group, cyclopropyl group, butyl group, isobutyl group, t-butyl group, cyclobutyl group, cyclopropylmethyl group, pentyl group, cyclopentyl group, or the like may be listed as examples.

The alkyl group is preferably a linear alkyl group, more preferably a $C_1$-$C_5$ linear alkyl group, further preferably a methyl group or an ethyl group, and particularly preferably a methyl.

When $R^1$ is an alkenyl group, the number of carbon atoms of the alkenyl group is 1 to 10, and preferably 1 to 6. The alkenyl group may be linear, may be branched, and may form a ring. For example, a halogen atom such as F, Cl, Br, or I, a hydroxyl group, or the like may be listed as examples of a substituent of the alkenyl group.

Groups in which one or two or more double bonds have been introduced into the group described above as the alkyl group may be listed as examples of the alkenyl group, such as a vinyl group, allyl group, or the like.

When $R^1$ is an aryl group, the number of carbon atoms of the aryl group is 6 to 14, and preferably 6 to 10. For example, a halogen atom such as F, Cl, Br, or I, a hydroxyl group, or the like may be listed as examples of a substituent of the aryl group. A phenyl group or the like may be listed as examples of the specific aryl group.

Furthermore, the compound represented by the foregoing formula (1) may be isotope labelled. The isotope is not particularly limited, and stable isotopes $^{13}$C, $^2$H(D), or the like may be listed as examples thereof. By performing isotope labeling, it is possible to change the in vivo kinetics of the compound or a pharmacologically acceptable salt thereof prior to performing the isotope labeling. For example, deuterium-labelled compounds represented by the following formulas (A), (B), and (C) may be listed as examples of this kind of compound.

[Formula 6]

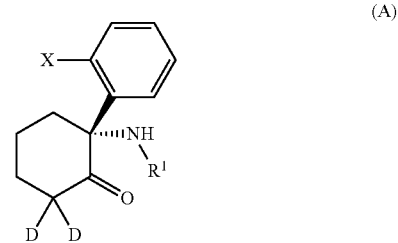

(A)

[In formula (A), X represents a hydrogen atom, a halogen atom, or a $C_1$-$C_{10}$ alkyl group that may be substituted; $R^1$ represents a $C_1$-$C_{10}$ alkyl group that may be substituted, a $C_1$-$C_{10}$ alkenyl group that may be substituted, or a $C_6$-$C_{14}$ aryl group that may be substituted; and D represents a deuterium atom.]

X and $R^1$ in the foregoing formula (A) are the same as X and $R^1$ in the foregoing formula (1).

[Formula 7]

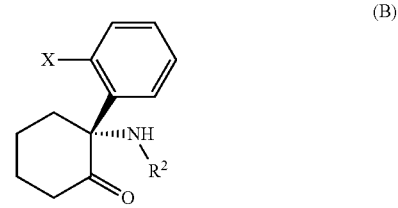

(B)

[In formula (B), X represents a hydrogen atom, a halogen atom, or a $C_1$-$C_{10}$ alkyl group that may be substituted; and $R^2$ represents a $C_1$-$C_{10}$ alkyl group that may be substituted, a $C_1$-$C_{10}$ alkenyl group that may be substituted, or a $C_6$-$C_{14}$ aryl group that may be substituted. Here, at least one of the hydrogen atoms contained in the groups represented by X and $R^2$ is a deuterium atom.]

X in the foregoing formula (B) is the same as X in the foregoing formula (1), and $R^2$ in the foregoing formula (B) is the same as $R^1$ in the foregoing formula (1).

[Formula 8]

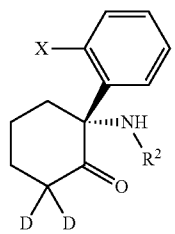

(C)

[In formula (C), X represents a hydrogen atom, a halogen atom, or a $C_1$-$C_{10}$ alkyl group that may be substituted; and $R^2$ represents a $C_1$-$C_{10}$ alkyl group that may be substituted, a $C_1$-$C_{10}$ alkenyl group that may be substituted, or a $C_6$-$C_{14}$ aryl group that may be substituted. Here, 0 or more of the hydrogen atoms contained in the groups represented by X and $R^2$ is a deuterium atom.]

X in the foregoing formula (C) is the same as X in the foregoing formula (1), and $R^2$ in the foregoing formula (C) is the same as $R^1$ in the foregoing formula (1).

In the preventative or therapeutic agent for an inflammatory disease of the present embodiment, hydrochloride, sulfate, hydrobromide, hydroiodide, phosphate, nitrate, benzoate, methanesulfonate, 2-hydroxyethane sulfonate, p-toluenesulfonate, acetate, propanoate, oxalate, malonate, succinate, glutarate, adipate, tartrate, maleate, fumarate, malate, mandelate, or the like may be listed as examples of the pharmacologically acceptable salt of the compound represented by the foregoing formula (1); hydrochloride, methanesulfonate, and p-toluenesulfonate are preferable, while hydrochloride is particularly preferable.

In the preventative or therapeutic agent for an inflammatory disease of the present embodiment, the compound represented by the foregoing formula (1) or a pharmacologically acceptable salt thereof may be a hydrate, or may be a solvate with the exception of a hydrate.

The preventative or therapeutic agent for an inflammatory disease of the present embodiment may contain as an active ingredient the compound represented by the foregoing formula (1), which is a free base; a pharmacologically acceptable salt of the compound represented by the foregoing formula (1); or both the compound represented by the foregoing formula (1) and a pharmacologically acceptable salt of the compound represented by the foregoing formula (1).

The compound represented by the foregoing formula (1) is preferably a compound represented by the following formula (2). That is, the preventative or therapeutic agent of the present embodiment preferably contains as an active ingredient the compound represented by the following formula (2) or a pharmacologically acceptable salt thereof. As will be described later in examples, the compound represented by the following formula (2) or a pharmacologically acceptable salt thereof is highly effective in preventing or treating an inflammatory disease.

[Formula 9]

(2)

[In formula (2), one or more hydrogen atoms may be substituted for deuterium atoms.]

The compound represented by the foregoing formula (2) is a compound wherein X and $R^1$ in the foregoing formula (1) are Cl and a methyl group, respectively, and the compound is called R-ketamine. That is, the preventative or therapeutic agent for an inflammatory disease of the present embodiment preferably contains as an active ingredient R-ketamine or a pharmacologically acceptable salt thereof.

Furthermore, as described above, the compound represented by the foregoing formula (2) may be isotope labelled. The isotope is not particularly limited, and stable isotopes $^{13}C$, $^2H(D)$, or the like may be listed as examples thereof. By performing isotope labeling, it is possible to change the in vivo kinetics of the compound or a pharmacologically acceptable salt thereof prior to performing the isotope labeling. For example, deuterium-labeled compounds represented by the following formulas (D), (E), and (F) may be listed as examples of this kind of compound.

[Formula 10]

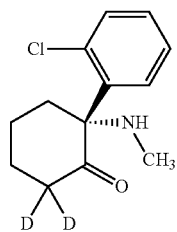

(D)

[In formula (D), D represents a deuterium atom.]

[Formula 11]

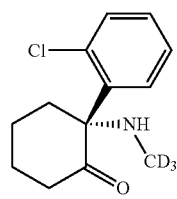

(E)

[In formula (E), D represents a deuterium atom.]

[Formula 12]

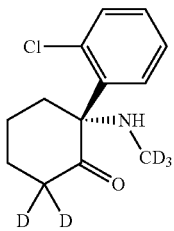

(F)

[In formula (F), D represents a deuterium atom.]

R-ketamine represented by the foregoing formula (2) is a free base. Hydrochloride is preferable as the pharmacologically acceptable salt of R-ketamine. The chemical formula of R-ketamine hydrochloride is shown in the following formula (5). In the preventative or therapeutic agent for an inflammatory disease of the present embodiment, R-ketamine or a pharmacologically acceptable salt thereof may be a hydrate, or may be a solvate with the exception of a hydrate.

[Formula 13]

(5)

Furthermore, R-ketamine or a pharmacologically acceptable salt thereof may be isotope-labelled. The isotope is not particularly limited, and stable isotopes $^{13}C$, $^{2}H(D)$, or the like may be listed as examples thereof. By performing isotope labeling, it is possible to change the in vivo kinetics of R-ketamine or a pharmacologically acceptable salt thereof prior to performing the isotope labeling. For example, deuterium-labeled R-ketamine hydrochloride represented by the following formula (6) is expected to have a slow metabolism and a long duration.

[Formula 14]

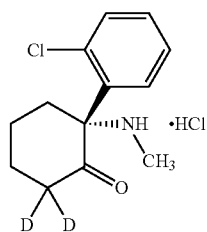

(6)

[In formula (6), D represents a deuterium atom.]

Furthermore, the preventative or therapeutic agent for an inflammatory disease of the present embodiment preferably does not substantially contain a compound represented by the following formula (3) or a pharmacologically acceptable salt thereof.

[Formula 15]

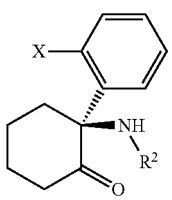

(3)

[In formula (3), X represents a hydrogen atom, a halogen atom, or a $C_1$-$C_{10}$ alkyl group that may be substituted; and $R^1$ represents a $C_1$-$C_{10}$ alkyl group that may be substituted, a $C_1$-$C_{10}$ alkenyl group that may be substituted, or a $C_6$-$C_{14}$ aryl group that may be substituted.]

In the preventative or therapeutic agent for an inflammatory disease of the present embodiment, "does not substantially contain a compound represented by the foregoing formula (3) or a pharmacologically acceptable salt thereof" means the preventative or therapeutic agent (i) does not contain the compound represented by the foregoing formula (3) at all, and also does not contain a pharmacologically acceptable salt of the compound represented by the foregoing formula (3) at all, (ii) may include the compound represented by the foregoing formula (3) or a pharmacologically acceptable salt of the compound represented by the foregoing formula (3) in an amount that does not cause side effects, or (iii) may include an amount of the compound represented by the foregoing formula (3) or a pharmacologically acceptable salt of the compound represented by the foregoing formula (3) to a degree that is unavoidable from the standpoint of production thereof.

More specifically, for example, in the preventative or therapeutic agent for an inflammatory disease of the present embodiment, the compound represented by the foregoing formula (1), which is a drug substance when regarded as a pharmaceutical product, or a pharmacologically acceptable salt thereof may contain the compound represented by the foregoing formula (3) or a pharmacologically acceptable salt thereof at an amount of 0.15 mol % or less.

The compound represented by the foregoing formula (3) or a pharmacologically acceptable salt thereof may be a compound represented by the following formula (4) or a pharmacologically acceptable salt thereof. That is, the preventative or therapeutic agent for an inflammatory disease of the present embodiment may not substantially contain a compound represented by the following formula (4) or a pharmacologically acceptable salt thereof.

[Formula 16]

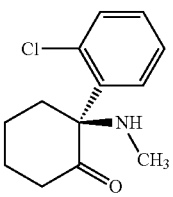

(4)

The compound represented by the foregoing formula (4) is a compound wherein X and $R^1$ in the foregoing formula (3) are Cl and a methyl group, respectively, and the compound is called S-ketamine. That is, the preventative or therapeutic agent for an inflammatory disease of the present embodiment preferably does not substantially contain S-ketamine or a pharmacologically acceptable salt thereof.

As will be described later in examples, the effect of preventing or treating an inflammatory disease when administering R-ketamine is higher than the effect of preventing or treating an inflammatory disease when administering S-ketamine. Furthermore, it is conceivable that the side effects of RS-ketamine (psychosis-inducing effects, dissociation symptoms, drug dependence, and the like), which is an equivalent mixture of R-ketamine and S-ketamine, are mainly caused by S-ketamine.

Accordingly, the preventative or therapeutic agent for an inflammatory disease that contains as an active ingredient the compound represented by the foregoing formula (1) or a pharmacologically acceptable salt thereof and does not substantially contain the compound represented by the foregoing formula (3) or a pharmacologically acceptable salt thereof has a high therapeutic effect and few side effects.

Pharmaceutical Composition for Preventing or Treating Inflammatory Disease

In one embodiment, the present embodiment provides a pharmaceutical composition for preventing or treating an inflammatory disease or a bone disease, wherein the pharmaceutical composition contains the above-described preventative or therapeutic agent for an inflammatory disease or a bone disease, and a pharmacologically acceptable carrier. The pharmaceutical composition for preventing or treating a bone disease will be described later.

The above-described preventative or therapeutic agent for an inflammatory disease is preferably formulated as a pharmaceutical composition. The pharmaceutical composition may be in a dosage form used orally, or may be in a dosage form used parenterally.

Tablets, capsules, coated tablets, troches, liquid medicines such as solutions or suspensions, and the like may be listed as examples of the dosage form used orally. Furthermore, injections, powders, drops, sprays, creams, suppositories, patches, liniments, gels, and the like may be listed as examples of the dosage form used parenterally. The formulations of these dosage forms may all be prepared according to a method known by a person having ordinary skill in the pharmaceutical art.

When preparing the pharmaceutical composition of the present embodiment as a formulation for injection, the form of a solution or suspension formulation is preferable. Furthermore, when preparing the pharmaceutical composition of the present embodiment as a formulation for transmucosal administration, such as in the nasal cavity or oral cavity, the form of a powder, drops, or aerosol formulation is preferable. Moreover, when preparing the pharmaceutical composition of the present embodiment as a formulation for rectal administration, the form of a semi-solid agent formulation, such as a cream or suppository, is preferable.

The pharmaceutically acceptable carrier is not particularly limited, and those used for ordinary pharmaceutical compositions may be used. For example, antioxidants, stabilizers, preservatives, flavoring agents, colorants, dissolving agents, solubilizers, surfactants, emulsifiers, defoamers, viscosity modifiers, gelling agents, absorption promoters, dispersants, excipients, pH adjusters, and the like may be listed as examples.

The pharmaceutical composition may further include an additive. Lubricants such as magnesium stearate, sweeteners such as sucrose, lactose, and saccharin, flavoring agents such as peppermint and gaultheria adenothrix oil, benzyl alcohol and phenol stabilizers, buffering agents such as buffered phosphate and sodium acetate, solubilizing agents such as benzyl benzoate and benzyl alcohol, antioxidants, preservatives, and the like may be given as examples of additives.

Furthermore, the pharmaceutical composition of the present embodiment may contain, in addition to the compound represented by the foregoing formula (1) or a pharmacologically acceptable salt thereof, another medicinal ingredient that has an anti-inflammatory effect other than the compound represented by the foregoing formula (1) or a pharmacologically acceptable salt thereof.

A formulation for injection may contain, for example, plasma-derived proteins such as albumin, amino acids such as glycine, sugars such as mannitol, and the like as the pharmaceutically acceptable carrier, and may also further contain a buffering agent, solubilizing agent, isotonic agent, and the like. Furthermore, when using it as an aqueous or lyophilized formulation, for example, it may contain a surfactant such as Tween (registered trademark) 80 and Tween (registered trademark) 20 to avoid agglutination.

Formulations for parenteral administration other than formulations for injection may, for example, contain distilled water or saline, polyalkylene glycol such as polyethylene glycol, oil of vegetable origin, hydrogenated naphthalene, or the like as the pharmaceutically acceptable carrier.

For example, a formulation for rectal administration, such as a suppository, may contain, for example, polyalkylene glycol, Vaseline, cocoa oil, or the like. Furthermore, a formulation for inhalation may be solid, and may contain, for example, lactose as an excipient. Moreover, drops for nasal administration may be an aqueous solution or an oil solution.

The exact dosage and administration schedule of the pharmaceutical composition of the present embodiment may be appropriately adjusted depending on the required amount, treatment method, disease, or degree of necessity for an individual treatment subject, and the like. Furthermore, the administration route is preferably oral administration, nasal administration or intravenous administration by injection, and subcutaneous administration or intramuscular administration.

The treatment target is not particularly limited, but is preferably a mammal, and more preferably a human.

Dosage may be determined according to, specifically, age, body weight, health status, sex, diet, administration time, administration method, excretion rate, drug combinations, the subject's medical condition, and the like, and furthermore, it may be determined in consideration of other factors.

When administering the pharmaceutical composition of the present embodiment to a patient having an inflammatory disease, it is preferable that the pharmaceutical composition includes an active ingredient (the compound represented by the foregoing formula (1) or a pharmacologically acceptable salt thereof) at an amount effective for reducing the symptoms of each inflammatory disease, and preferably for reducing the inflammation of each inflammatory disease.

Although the dosage per day of the compound represented by the foregoing formula (1) or a pharmacologically acceptable salt thereof will differ depending on the state and weight of a patient, the type of compound, the administration route, and the like, when administering orally, the dosage is usually about 0.01 to 1,000 mg/person/day, and preferably 0.1 to 500 mg/person/day; furthermore, when administering parenterally, the dosage is usually about 0.01 to 500 mg/person/day, and preferably 0.1 to 100 mg/person/day. It is considered appropriate to administer the pharmaceutical composition of the present embodiment once a day or in several divided doses.

The pharmaceutical composition of the present embodiment may also be used to prevent an inflammatory disease by administering before the onset of an inflammatory disease, and may also be used to treat an inflammatory disease by administering after the onset of symptoms of an inflammatory disease.

Preventative or Therapeutic Agent for Bone Disease

In one embodiment, the present invention provides a preventative or therapeutic agent for a bone disease, containing as an active ingredient a compound represented by the following formula (1) or a pharmacologically acceptable salt thereof. As will be described later in examples, it is possible to prevent or treat a bone disease with the preventative or therapeutic agent of the present embodiment.

[Formula 17]

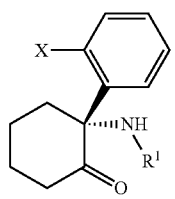

(1)

[In formula (1), X represents a hydrogen atom, a halogen atom, or a $C_1$-$C_{10}$ alkyl group that may be substituted; and $R^1$ represents a $C_1$-$C_{10}$ alkyl group that may be substituted, a $C_1$-$C_{10}$ alkenyl group that may be substituted, or a $C_6$-$C_{14}$ aryl group that may be substituted.]

In the preventative or therapeutic agent of the present embodiment, osteoporosis, osteolytic bone metastasis, Paget's disease of the bone, and the like may be listed as examples of a "bone disease." As will be described later in examples, administering the preventative or therapeutic agent of the preventative or therapeutic agent makes it possible to change the balance between bone resorption by osteoclasts and bone formation by osteoblasts so that bone formation is superior. As a result, it is possible to prevent or treat a bone disease.

In the compound represented by the foregoing formula (1), X and $R^1$ may be the same as that in the above-described preventative or therapeutic agent for an inflammatory disease. Furthermore, the pharmacologically acceptable salt of the compound represented by the foregoing formula (1) may be the same as that in the above-described preventative or therapeutic agent for an inflammatory disease.

In the preventative or therapeutic agent for a bone disease of the present embodiment, the compound represented by the foregoing formula (1) is preferably a compound represented by the following formula (2). That is, the preventative or therapeutic agent for a bone disease of the present embodiment preferably contains as an active ingredient the compound represented by the following formula (2) or a pharmacologically acceptable salt thereof. As will be described in examples, the compound represented by the following formula (2) or a pharmacologically acceptable salt thereof is highly effective in preventing or treating a bone disease.

[Formula 18]

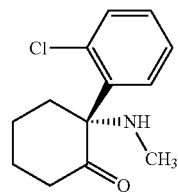

(2)

The compound represented by the foregoing formula (2) is a compound wherein X and $R^1$ in the foregoing formula (1) are Cl and a methyl group, respectively, and the compound is called R-ketamine. That is, the preventative or therapeutic agent for a bone disease of the present embodiment preferably contains as an active ingredient R-ketamine or a pharmacologically acceptable salt thereof.

R-ketamine represented by the foregoing formula (2) is a free base. Hydrochloride is preferable as the pharmacologically acceptable salt of R-ketamine. The chemical formula of R-ketamine hydrochloride is shown in the following formula (5). In the preventative or therapeutic agent for a bone disease of the present embodiment, R-ketamine or a pharmacologically acceptable salt thereof may be a hydrate, or may be a solvate with the exception of a hydrate.

[Formula 19]

(5)

Furthermore, R-ketamine or a pharmacologically acceptable salt thereof may be isotope-labelled. The isotope is not particularly limited, and stable isotopes $^{13}C$, $^{2}H(D)$, or the like may be listed as examples thereof. By performing isotope labeling, it is possible to change the in vivo kinetics of R-ketamine or a pharmacologically acceptable salt thereof prior to performing the isotope labeling. For example, deuterium-labeled R-ketamine hydrochloride represented by the following formula (6) is expected to have a slow metabolism and a long duration.

[Formula 20]

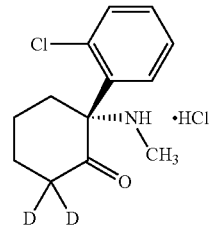

(6)

[In formula (6), D represents a deuterium atom.]

Furthermore, the preventative or therapeutic agent for a bone disease of the present embodiment preferably does not substantially contain a compound represented by the following formula (3) or a pharmacologically acceptable salt thereof.

[Formula 21]

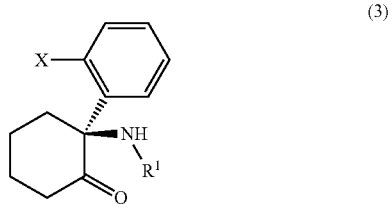

(3)

[In formula (3), X represents a hydrogen atom, a halogen atom, or a $C_1$-$C_{10}$ alkyl group that may be substituted; and $R^1$ represents a $C_1$-$C_{10}$ alkyl group that may be substituted, a $C_1$-$C_{10}$ alkenyl group that may be substituted, or a $C_6$-$C_{14}$ aryl group that may be substituted.]

In the preventative or therapeutic agent for a bone disease of the present embodiment, "does not substantially contain a compound represented by the foregoing formula (3) or a pharmacologically acceptable salt thereof" means the preventative or therapeutic agent (i) does not contain the compound represented by the foregoing formula (3) at all, and also does not contain a pharmacologically acceptable salt of the compound represented by the foregoing formula (3) at all, (ii) may include the compound represented by the foregoing formula (3) or a pharmacologically acceptable salt of the compound represented by the foregoing formula (3) in an amount that does not cause side effects, or (iii) may include an amount of the compound represented by the foregoing formula (3) or a pharmacologically acceptable salt of the compound represented by the foregoing formula (3) to a degree that is unavoidable from the standpoint of production thereof.

More specifically, for example, in the preventative or therapeutic agent for a bone disease of the present embodiment, the compound represented by the foregoing formula (1), which is a drug substance when regarded as a pharmaceutical product, or a pharmacologically acceptable salt thereof may contain the compound represented by the foregoing formula (3) or a pharmacologically acceptable salt thereof at an amount of 0.15 mol % or less.

The compound represented by the foregoing formula (3) or a pharmacologically acceptable salt thereof may be a compound represented by the following formula (4) or a pharmacologically acceptable salt thereof. That is, the preventative or therapeutic agent for a bone disease of the present embodiment preferably does not substantially contain a compound represented by the following formula (4) or a pharmacologically acceptable salt thereof.

[Formula 22]

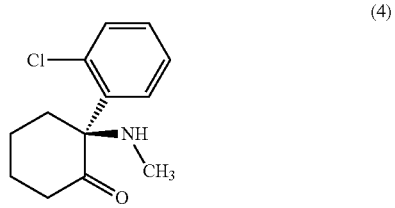

(4)

The compound represented by the foregoing formula (4) is a compound wherein X and $R^1$ in the foregoing formula (3) are Cl and a methyl group, respectively, and the compound is called S-ketamine. That is, the preventative or therapeutic agent for a bone disease of the present embodiment preferably does not substantially contain S-ketamine or a pharmacologically acceptable salt thereof.

As will be described later in examples, the effect of preventing or treating a bone disease when administering R-ketamine is higher than the effect of preventing or treating a bone disease when administering S-ketamine. Furthermore, as described above, it is conceivable that the side effects of RS-ketamine, which is an equivalent mixture of R-ketamine and S-ketamine, are mainly caused by S-ketamine.

Accordingly, the preventative or therapeutic agent for a bone disease that contains as an active ingredient the compound represented by the foregoing formula (1) or a pharmacologically acceptable salt thereof and does not substantially contain the compound represented by the foregoing formula (3) or a pharmacologically acceptable salt thereof has a high therapeutic effect and few side effects.

Pharmaceutical Composition for Preventing or Treating Bone Disease

In one embodiment, the present embodiment provides a pharmaceutical composition for preventing or treating a bone disease, containing the above-described preventative or therapeutic agent for a bone disease, and a pharmacologically acceptable carrier.

The above-described preventative or therapeutic agent for a bone disease is preferably formulated as a pharmaceutical composition. The pharmaceutical composition may be in a dosage form used orally, or may be in a dosage form used parenterally.

The dosage form of the pharmaceutical composition for preventing or treating a bone disease of the present embodiment may be the same as the above-described pharmaceutical composition for preventing or treating an inflammatory disease.

Furthermore, the pharmaceutical composition of the present embodiment may contain, in addition to the compound represented by the foregoing formula (1) or a pharmacologically acceptable salt thereof, another medicinal ingredient that has the effect of preventing or treating a bone disease other than the compound represented by the foregoing formula (1) or a pharmacologically acceptable salt thereof. For example, calcium, magnesium, vitamin D, calcitocin, vitamin K2, anti-RANKL preparation, biologics (antibody drug), and the like may be listed as examples as such an ingredient.

The exact dosage and administration schedule of the pharmaceutical composition of the present embodiment may be appropriately adjusted depending on the required amount, treatment method, disease, or degree of necessity for an individual treatment subject, and the like. Furthermore, the administration route is preferably oral administration, nasal administration or intravenous administration by injection, and subcutaneous administration or intramuscular administration.

The treatment target is not particularly limited, but is preferably a mammal, and more preferably a human.

Dosage may be determined according to, specifically, age, body weight, health status, sex, diet, administration time, administration method, excretion rate, drug combinations, the subject's medical condition, and the like, and furthermore, it may be determined in consideration of other factors.

When administering the pharmaceutical composition of the present embodiment to a patient having a bone disease, it is preferable that the pharmaceutical composition includes an active ingredient (the compound represented by the foregoing formula (1) or a pharmacologically acceptable salt thereof) at an amount effective for reducing the symptoms of each bone disease.

Although the dosage per day of the compound represented by the following formula (1) or a pharmacologically acceptable salt thereof will differ depending on the state and weight of a patient, the type of compound, the administration route, and the like, when administering orally, the dosage is usually about 0.01 to 1,000 mg/person/day, and preferably 0.1 to 500 mg/person/day; furthermore, when administering parenterally, the dosage is usually about 0.01 to 500 mg/person/day, and preferably 0.1 to 100 mg/person/day. It is considered appropriate to administer the pharmaceutical composition of the present embodiment once a day or in several divided doses.

The pharmaceutical composition of the present embodiment may also be used to prevent a bone disease by administering before the onset of a bone disease, and may also be used to treat a bone disease by administering after the onset of symptoms of a bone disease.

Other Embodiments

In one embodiment, the present invention provides a method for preventing or treating an inflammatory disease or a bone disease, including administering an effective amount of the compound represented by the foregoing formula (1) or a pharmacologically acceptable salt thereof to a patient in need of treatment.

In one embodiment, the present invention provides the compound represented by the foregoing formula (1) or a pharmacologically acceptable salt thereof for preventing or treating an inflammatory disease or a bone disease.

In one embodiment, the present invention provides a use for the compound represented by the foregoing formula (1) or a pharmacologically acceptable salt thereof for producing a preventative or therapeutic agent for an inflammatory disease or a bone disease.

In each of these embodiments, the compound represented by the foregoing formula (1), the pharmacologically acceptable salt of the compound represented by the foregoing formula (1), the inflammatory diseases, and the bone diseases are the same as that which is described above. The compound represented by the foregoing formula (1) or a pharmacologically acceptable salt thereof preferably does not substantially contain the compound represented by the foregoing formula (3) or a pharmacologically acceptable salt thereof.

EXAMPLES

Hereinafter, the present invention will be described more specifically with reference to examples; however, the present invention is not limited to the following examples. Furthermore, various modifications may be made within a scope that does not depart from the technical idea of the present invention. All tests were performed with the consent of the Animal Ethics Committee of Chiba University.

Experimental Example 1

(Inflammatory Disease Model Mice)

R-ketamine and S-ketamine were administered to inflammatory disease model mice and the therapeutic effect was examined. Ulcerative colitis model mice to which dextran sulfate (DSS) was administered were used as inflammatory disease model mice.

R-ketamine hydrochloride was used as R-ketamine. Furthermore, S-ketamine hydrochloride was used as S-ketamine. R-ketamine hydrochloride and S-ketamine hydrochloride were prepared from RS-ketamine (Ketalar (registered trademark), ketamine hydrochloride, Daiichi Sankyo Co., Ltd.) using D-tartaric acid or L-tartaric acid according to the method described in U.S. Pat. No. 6,040,479.

A purity of each isomer was confirmed by high performance liquid chromatography (CHIRALPAK (registered trademark) IA, Daicel Corporation, column size: 250×4.6 mm, mobile phase: n-hexane/dichloromethane/diethylamine (75/25/0.1), S-ketamine retention time=6.99 minutes, R-ketamine retention time=10.56 minutes).

As a result, the purity of the prepared S-ketamine was 99% or more. Furthermore, the purity of R-ketamine was 99% or more.

Preparation of ulcerative colitis model mice and administration of drugs were performed as follows. FIG. 1 is a schematic diagram describing an experimental schedule. Male BALB/cCr Slc mice (6 weeks old, Japan SLC, Inc.) were used as mice. The mice were given free access to water and food.

The experiment was started when the mice reached 7 weeks old. Along with the start of the experiment, tap water supplemented with 3% DSS was given as drinking water. Furthermore, a group to which normal tap water containing no DSS was given as drinking water was prepared as a control group.

From the 1st day of the experiment, the mice in the group given tap water supplemented with 3% DSS were administered intraperitoneally once a day for 14 days along with saline (10 mL/kg body weight), S-ketamine (10 mg/kg body weight), or R-ketamine (10 mg/kg body weight). From the 1st day of the experiment, the mice in the control group were intraperitoneally administered saline (10 mL/kg body weight) once a day for 14 days.

Subsequently, on the 15th day from the start of the experiment, the mice in each group were anesthetized with 5% isoflurane and blood was collected from the heart to obtain plasma. Plasma was stored in a freezer at −80° C. until measurement of inflammatory cytokine, to be described later. Furthermore, after the blood collection was completed, the mice in each group were euthanized by exsanguination under isoflurane anesthesia.

Experimental Example 2

(Evaluation of Disease Condition Score of Inflammatory Disease Model Mice)

For the mice in each group bred according to the schedule of Experimental Example 1, a disease condition score was calculated on the 7th day, 10th day, 12th day, and 14th day from the start of the experiment. The disease condition score was evaluated before administering saline, S-ketamine, or R-ketamine to the mice. Specifically, an evaluation score of the amount of weight loss, an evaluation score of feces, and an evaluation score of bleeding were obtained according to the following evaluation criteria, and the total score was used as the disease condition score.

<<Evaluation Score of Amount of Weight Loss>>

Body weight before administration of saline, S-ketamine, or R-ketamine was set to 100%, and an amount of weight loss of the mice in each group was evaluated according to the evaluation criteria described in Table 1 below.

TABLE 1

| Evaluation of Amount of Weight Loss | Score |
| --- | --- |
| Less than 0% | 0 |
| 0% or more, less than 5% | 1 |
| 5% or more, less than 10% | 2 |
| 10% or more, less than 20% | 3 |
| 20% or more | 4 |

<<Evaluation Score of Feces>>

Feces of the mice in each group were evaluated according to the evaluation criteria described in Table 2 below.

TABLE 2

| Evaluation of Feces | Score |
| --- | --- |
| Normal. Feces remained solid. | 0 |
| Loose stool. Feces were semi-solid. Damp and broke easily when touched. | 2 |
| Diarrhea. Feces were liquid. | 4 |

<<Evaluation of Bleeding>>

Bleeding of the mice in each group was evaluated according to the evaluation criteria described in Table 3 below.

TABLE 3

| Evaluation of Bleeding | Score |
| --- | --- |
| Normal. Blood was not mixed in feces. | 0 |
| Occult blood. Blood was mixed in feces. Slight staining around the anus. | 2 |
| Melena. Blood was mixed in feces. Area around the anus was stained with blood. | 4 |

<<Disease Condition Score>>

FIG. 2 is a graph showing the disease condition score of the mice in each group. In FIG. 2, "control" shows the results of the mice in the control group, "DSS+saline" shows the results of the mice in the group administered DSS and saline, "DSS+S-ketamine" shows the results of the mice in the group administered DSS and S-ketamine, and "DSS+R-ketamine" shows the results of the mice in the group administered DSS and R-ketamine.

In FIG. 2, the data are represented by mean±standard error (n=8 to 9 mice/group). Statistical analysis was implemented by performing a one-way analysis of variance (one-way ANOVA) followed by a least significant difference test (Fisher LSD test). In FIG. 2, "*," "," and "*" show that a significant difference was observed at "p<0.05," "p<0.01," and "p<0.001," respectively, as compared to the group administered "DSS+S-ketamine."

As a result, a significant deterioration of the disease condition score was observed in the mice of the "DSS+saline" group as compared to the mice of the "control" group. Furthermore, an improvement tendency of the disease condition score was observed in the "DSS+S-ketamine" group, but it was not significant. On the other hand, a significant improvement of the disease condition score was observed in the "DSS+R-ketamine" group.

Experimental Example 3

(Evaluation of Colonic Inflammation Score of Inflammatory Disease Model Mice)

In Experimental Example 1, the colonic inflammation score was evaluated for the mice in each group euthanized on the 15th day from the start of the experiment.

The mice from each group that had been euthanized were resected from cecum to anus, and a length from directly below the cecum to the anus was measured. Subsequently, the lumen of the colon was washed with saline, and after washing, an incision was made in the longitudinal direction, and a colonic inflammation score was determined according to the following evaluation criteria.

TABLE 4

| Evaluation of Colonic Inflammation | Score |
| --- | --- |
| No injuries were observed. | 0 |
| Hyperemia was observed. | 1 |
| Hyperemia and thickening of the wall were observed. | 2 |
| No ulcers were observed. | |
| An ulcer was observed, but there was no thickening. | 3 |
| Multiple ulcers or sites of inflammation were observed. | 4 |

FIG. 3 is a graph showing the colonic inflammation scores of the mice in each group. In FIG. 3, "control" shows the results of the mice in the control group, "DSS+saline" shows the results of the mice in the group administered DSS and saline, "DSS+S-ketamine" shows the results of the mice in the group administered DSS and S-ketamine, and "DSS+R-ketamine" shows the results of the mice in the group administered DSS and R-ketamine.

The data are represented by mean±standard error (n=8 to 9 mice/group). Statistical analysis was implemented by performing a one-way analysis of variance (one-way ANOVA) followed by a least significant difference test (Fisher LSD test). In FIG. 3, "*" and "***" show that a significant difference was observed at "p<0.05" and "p<0.001," respectively, as compared to the group administered DSS+S-ketamine. Furthermore, "+++" shows that a significant difference was observed at "p<0.001" as compared to the "DSS+S-ketamine" group.

As a result, a significant deterioration of the colonic inflammation score was observed in the mice of the "DSS+saline" group as compared to the mice of the "control" group. Furthermore, a significant improvement of the colonic inflammation score was observed in the "DSS+R-ketamine" group as compared to the "DSS+S-ketamine" group.

Experimental Example 4

(Evaluation of Inflammatory Cytokines in Blood)

In Experimental Example 1, inflammatory cytokines in plasma collected from the mice of each group on the 15th day from the start of the experiment were quantified. Interleukin (IL)-6 was quantified as the inflammatory cytokine. IL-6 was quantified by ELISA method using a commercially available kit.

FIG. 4 is a graph showing the results of quantifying IL-6 in blood. In FIG. 4, "control" shows the results of the mice in the control group, "DSS+saline" shows the results of the mice in the group administered DSS and saline, "DSS+S- ketamine" shows the results of the mice in the group administered DSS and S-ketamine, and "DSS+R-ketamine" shows the results of the mice in the group administered DSS and R-ketamine.

The data are represented by mean±standard error (n=8 to 9 mice/group). Statistical analysis was implemented by performing a one-way analysis of variance (one-way ANOVA) followed by a least significant difference test (Fisher LSD test). In FIG. 4, "" and "*" show that a significant difference was observed at "p<0.01" and "p<0.001," respectively, as compared to the "DSS+saline" group.

As a result, a significant increase of IL-6 concentration in blood was observed in the mice of the "DSS+saline" group as compared to the mice of the "control" group. Furthermore, a significant decrease of IL-6 concentration in blood was observed in the "DSS+S-ketamine" group and the "DSS+R-ketamine" group. Moreover, it was revealed that the effect of reducing IL-6 in blood by administration of R-ketamine was higher than when administering S-ketamine.

From the results of Experimental Examples 1 to 4, it was revealed that intraperitoneal administration of a 10 mg/kg dose of R-ketamine exhibited a therapeutic effect in DSS-treated mice, the ulcerative colitis animal model. In contrast to this, it was revealed that intraperitoneal administration of a 10 mg/kg dose of S-ketamine exhibited a tendency for a therapeutic effect in the ulcerative colitis animal model, but the effect was weaker than that of R-ketamine.

Since the pharmacokinetics of both isomers of ketamine are the same, it was considered that the difference in the therapeutic effect between R-ketamine and S-ketamine was not due to the difference in the pharmacokinetics of these isomers.

Furthermore, S-ketamine has a stronger affinity for NMDA receptors than R-ketamine. Therefore, it was speculated that the therapeutic effect of R-ketamine in DSS-treated mice, the ulcerative colitis animal model, is due to a mechanism other than NMDA receptor blockade.

Experimental Example 5

(Production of Social Defeat Stress Model Mice)

First, model mice subjected to stress, called "social defeat stress," were prepared by a known method. Specifically, one each of a C57/B6 male mouse (7 weeks old, Japan SLC, Inc.) and an ICR male mouse (9 weeks old or older, Japan SLC, Inc.) were made to coexist for a 10-day period. Each mouse was given free access to water and food. Since ICR mice are larger and more aggressive than C57/B6 mice, C57/B6 sustains stress when these mice are made to coexist.

Subsequently, C57/B6 mice subjected to social defeat stress were submitted to a social interaction test. As a result, about ¾ of the mice exhibited depressive symptoms, and the rest did not exhibit depressive symptoms. Subsequently, as a result of the social interaction test, the mice exhibiting depressive symptoms were selected, and a tail suspension test (Tail Suspension Test, TST), a forced swimming test (Forced Swimming Test, FST), and a sucrose preference test were performed. As a result, it was confirmed that the mice exhibiting depressive symptoms in the social interaction test exhibited more depressive symptoms according to the results of the TST, FST, and sucrose preference tests.

Experimental Example 6

(Examination of the Effect of R-Ketamine Administration on Social Defeat Stress Model Mice)

R-ketamine and S-ketamine were administered to mice having depressive symptoms (hereinafter sometimes referred to as "social defeat stress mice") prepared in Experimental Example 5, and the effects thereof were examined. R-ketamine hydrochloride was used as R-ketamine. Furthermore, S-ketamine hydrochloride was used as S-ketamine. R-ketamine hydrochloride and S-ketamine hydrochloride were prepared in the same manner as in Experimental Example 1.

R-ketamine (10 mg/kg body weight), S-ketamine (10 mg/kg body weight), or saline (10 mL/kg body weight) was intraperitoneally administered once to social defeat stress mice. Furthermore, C57/B6 male mice not subjected to "social defeat stress" were used as control mice. Saline (10 mL/kg body weight) was intraperitoneally administered once to the control mice.

Four days after administration of saline, R-ketamine, or S-ketamine, each mouse was anesthetized by inhalation of isoflurane. Subsequently, blood was collected and immediately centrifuged to obtain plasma. Plasma was stored in a freezer at −80° C. until measurement.

Subsequently, the concentrations of osteoprotegerin (Osteoprotegerin, hereinafter referred to as "OPG"), RANKL, and osteopontin (osteopontin, hereinafter referred to as "OPN") in each plasma were measured using an ELISA kit (R&D Systems, Inc.).

Figure 5:
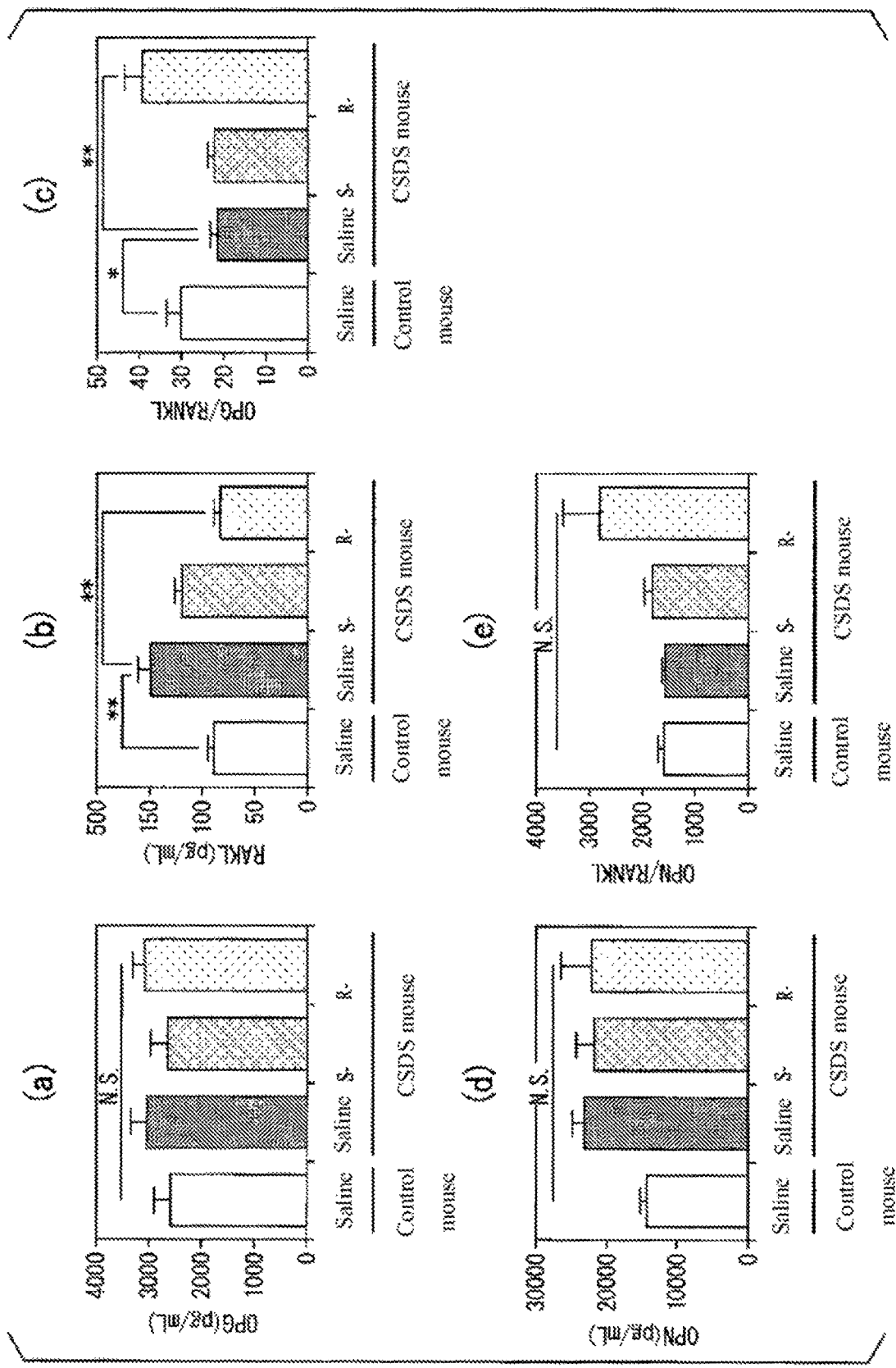
FIG. 5 (a) to (e) are graphs showing the results of Experimental Example 6.

FIG. 5 (a) to (e) are graphs showing the measurement results. FIG. 5 (a) shows the measurement results of OPG, FIG. 5 (b) shows the measurement results of RANKL, FIG. 5 (c) shows the OPG/RANKL ratio calculated based on the results of FIG. 5 (a) and (b), FIG. 5 (d) shows the measurement results of OPN, and FIG. 5 (e) shows the OPN/RANKL ratio calculated based on the results of FIGS. 5 (b) and (d). In FIG. 5 (a) to (e), the data are shown by mean±standard error (n=6 mice/group), "CSDS mouse" shows mice that exhibited depressive symptoms due to social defeat stress, "saline" shows the results of mice administered saline, "S-ketamine" shows the results of mice administered S-ketamine, and "R-ketamine" shows the results of mice administered R-ketamine.

Statistical analysis was implemented by performing a one-way analysis of variance followed by a least significant difference test. In FIGS. 5 (b) and (c), "*" shows there is a significant difference at p<0.05 as compared to the social defeat stress mouse group administered saline, and "**" shows there is a significant difference at p<0.01 as compared to the social defeat stress mouse group administered saline. Furthermore, in FIGS. 5 (a), (d), and (e), "N.S." showed no significant difference.

As a result, as shown in FIG. 5 (b), the social defeat stress mice were found to have significantly higher RANKL concentrations in plasma as compared to the control mice. Furthermore, it was revealed that when administering R-ketamine to social defeat stress mice, RANKL concentration in plasma was significantly decreased as compared to when saline was administered to social defeat stress mice.

On the other hand, even when S-ketamine was administered to social defeat stress mice, a significant change to RANKL concentration in plasma was not observed as compared to when saline was administered to social defeat stress mice.

As described above, bone homeostasis is maintained by a delicate balance between bone resorption by osteoclasts and bone formation by osteoblasts. An OPG/RANKL ratio is a marker used as an indicator of the balance between bone formation and bone resorption. As shown in FIG. 5 (c), it was revealed that the OPG/RANKL ratio of the social defeat stress mice administered saline was significantly decreased as compared to the control mice. A low OPG/RANKL ratio indicates that bone destruction and resorption tend to be superior to bone formation.

Moreover, it was revealed that when administering R-ketamine to social defeat stress mice, the OPG/RANKL ratio was significantly increased as compared to when saline was administered to social defeat stress mice. On the other hand, even when S-ketamine was administered to social defeat stress mice, a significant change to the OPG/RANKL ratio was not observed as compared to when saline was administered to social defeat stress mice.

Note that as shown in FIGS. 5 (d) and (e), no significant differences in OPN concentration in plasma and the OPN/RANKL ratio were observed.

From the above results, it was revealed that administration of R-ketamine is able to restore an abnormally high expression of RANKL to a normal value. This result shows that R-ketamine is useful as a preventive or therapeutic agent for bone diseases. In contrast to this, such an effect was not observed for S-ketamine.

Experimental Example 7

(Inflammatory Disease Model Mice)
Saline, 5-aminosalicylic acid (5-ASA), which is a standard drug for ulcerative colitis, or R-ketamine were each administered to inflammatory disease model mice, and the therapeutic effect was examined. Ulcerative colitis model mice to which dextran sulfate (DSS) was administered, the same as in Experimental Example 1, were used as inflammatory disease model mice. R-ketamine hydrochloride prepared in the same way as Experimental Example 1 was used as R-ketamine.

Figure 6:
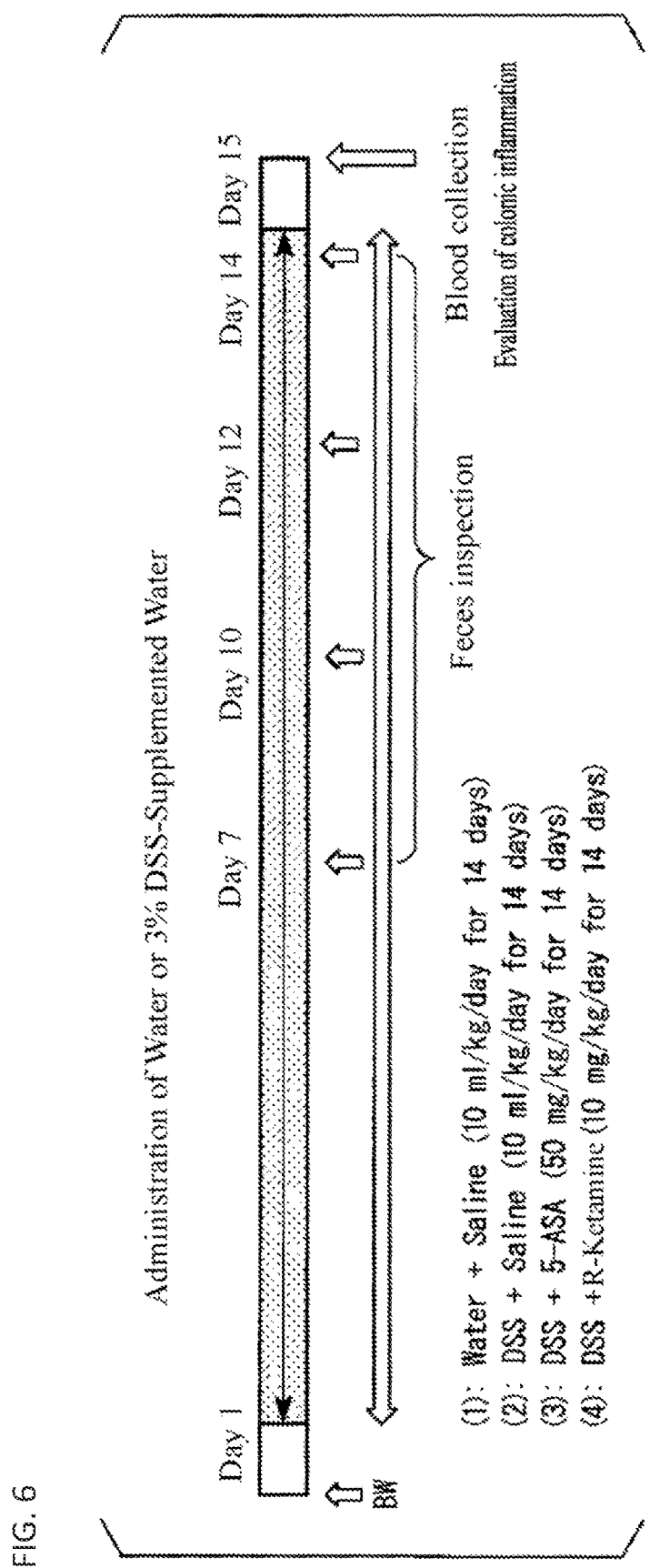
FIG. 6 A schematic diagram describing the experimental schedule of Experimental Example 7.

Preparation of ulcerative colitis model mice and administration of drugs were performed as follows. FIG. 6 is a schematic diagram describing an experimental schedule. Male BALB/cCr Slc mice (6 weeks old, Japan SLC, Inc.) were used as mice. The mice were given free access to water and food.

The experiment was started when the mice reached 7 weeks old. Along with the start of the experiment, tap water supplemented with 3% DSS was given as drinking water. Furthermore, a group to which normal tap water containing no DSS was given as drinking water was prepared as a control group.

From the 1st day of the experiment, the mice in the group given tap water supplemented with 3% DSS were administered intraperitoneally once a day for 14 days along with saline (10 mL/kg body weight), 5-ASA (50 mg/kg body weight), or R-ketamine (10 mg/kg body weight). From the 1st day of the experiment, the mice in the control group were intraperitoneally administered saline (10 mL/kg body weight) once a day for 14 days.

Subsequently, on the 15th day from the start of the experiment, the mice in each group were anesthetized with 5% isoflurane and blood was collected from the heart to obtain plasma. Plasma was stored in a freezer at −80° C. until measurement of inflammatory cytokine, to be described later. Furthermore, after blood collection was completed, the mice in each group were euthanized by exsanguination under isoflurane anesthesia.

Experimental Example 8

(Evaluation of Disease Condition Score of Inflammatory Disease Model Mice)
For mice in each group bred according to the schedule of Experimental Example 7, the disease condition score was calculated on the $7^{th}$ day, 10th day, 12th day, and 14th day from the start of the experiment. The disease condition score was evaluated before administering saline, 5-ASA, or R-ketamine to the mice. Specifically, the evaluation score of the amount of weight loss, the evaluation score of feces, and the evaluation score of bleeding were obtained according to the same evaluation criteria as Experimental Example 2, and the total score was used as the disease condition score.

Figure 7:
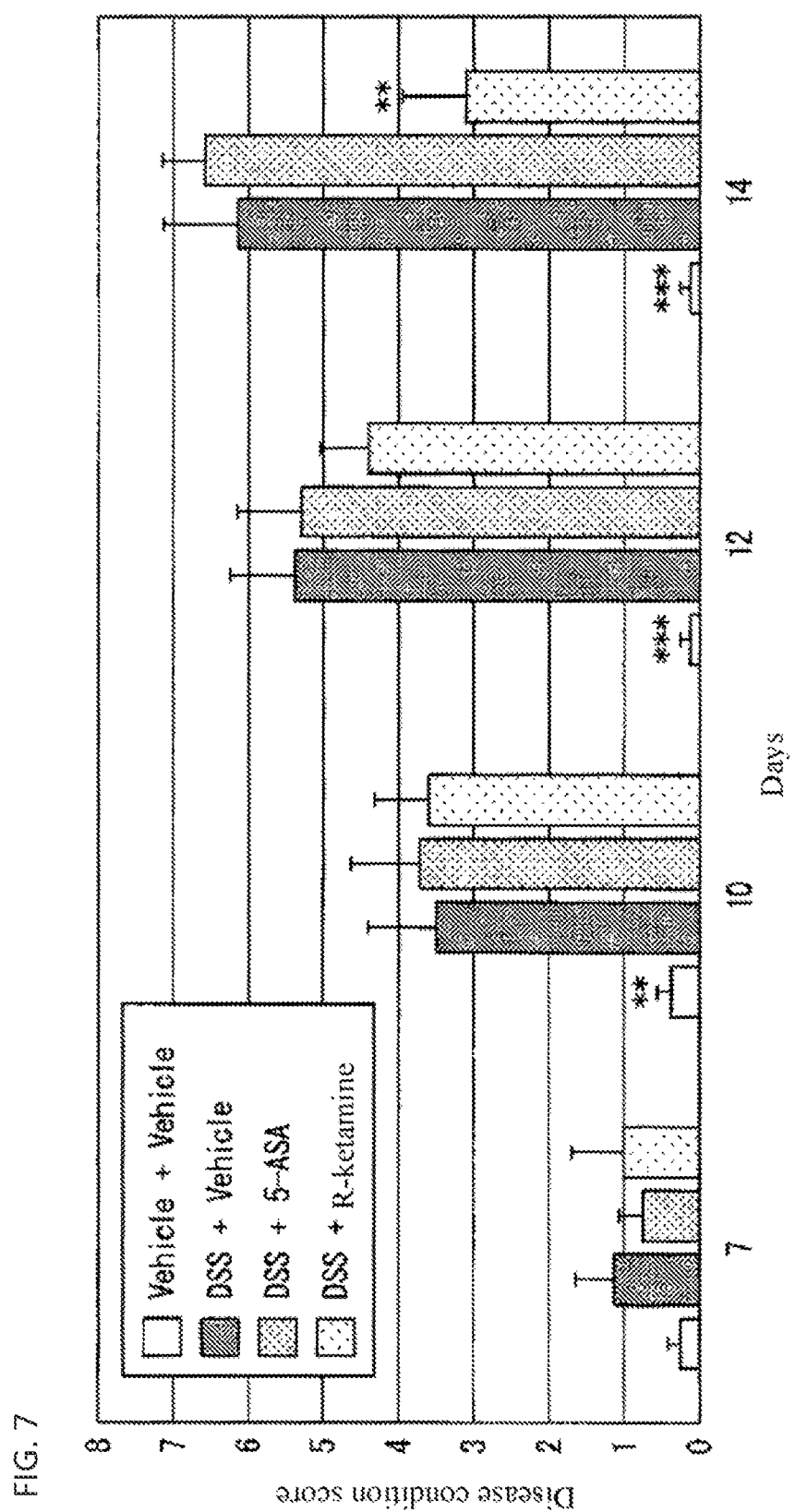
FIG. 7 A graph showing the results of Experimental Example 8.

FIG. 7 is a graph showing the disease condition score of the mice in each group. In FIG. 2, "Vehicle+Vehicle" shows the results of the mice in the control group, "DSS+Vehicle" shows the results of the mice in the group administered DSS and saline, "DSS+5-ASA" shows the results of the mice in the group administered DSS and 5-ASA, and "DSS+R-ketamine" shows the results of the mice in the group administered DSS and R-ketamine.

In FIG. 7, the data are represented by mean±standard error (n=8 to 10 mice/group). Statistical analysis was implemented by performing a one-way analysis of variance (one-way ANOVA) followed by a least significant difference test (Fisher LSD test). In FIG. 7, "" and "*" show that significant differences were observed at "p<0.01" and "p<0.001," respectively, as compared to the group administered DSS and saline.

As a result, a significant deterioration of the disease condition score was observed in the mice of the "DSS+saline" group as compared to the mice of the "control" group. Furthermore, an improvement tendency of the disease condition score was observed in the "DSS+5-ASA" group, but it was not significant. On the other hand, a significant improvement of the disease condition score was observed in the "DSS+R-ketamine" group.

Experimental Example 9

(Evaluation of Colonic Inflammation Score of Inflammatory Disease Model Mice)
The colonic inflammation score was evaluated for the mice in each group euthanized on the 15th day from the start of the experiment in Experimental Example 7.

The mice from each group that had been euthanized were resected from the cecum to the anus, and the length from directly below the cecum to the anus was measured. Subsequently, the lumen of the colon was washed with saline, and after washing, an incision was made in the longitudinal direction, and the colonic inflammation score was determined according to the same evaluation criteria as Experimental Example 3.

Figure 8:
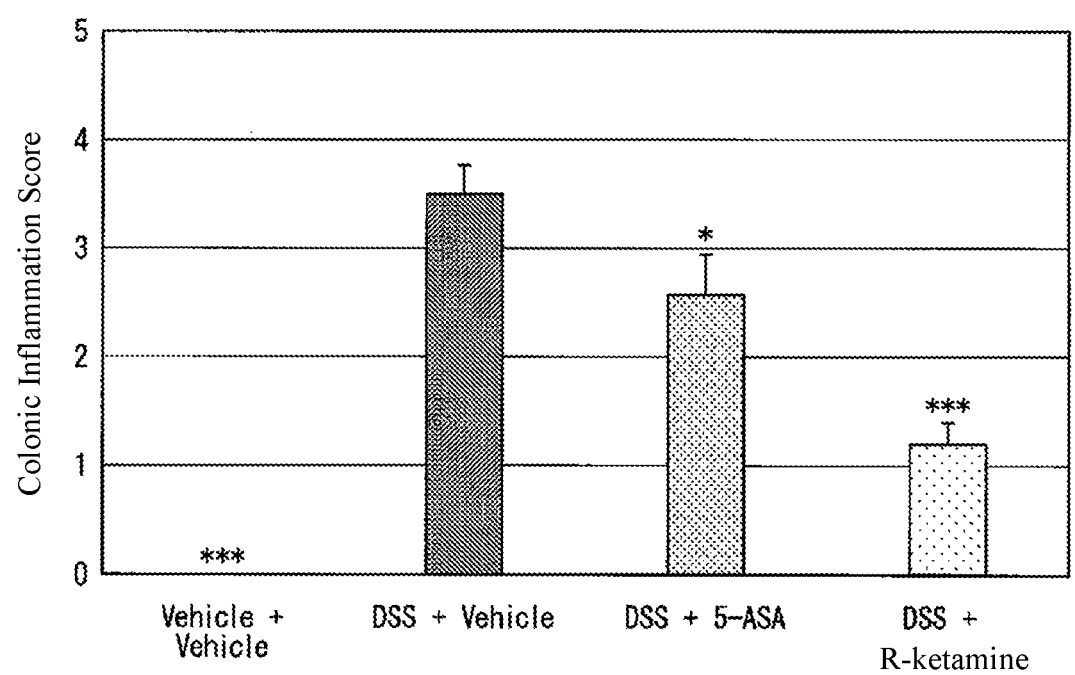
FIG. 8 A graph showing the results of Experimental Example 9.

FIG. 8 is a graph showing the colonic inflammation scores of mice in each group. In FIG. 8, "Vehicle+Vehicle" shows the results of the mice in the control group, "DSS+Vehicle" shows the results of the mice in the group administered DSS and saline, "DSS+5-ASA" shows the results of the mice in the group administered DSS and 5-ASA, and "DSS+R-ketamine" shows the results of the mice in the group administered DSS and R-ketamine.

The data are represented by mean±standard error (n=8 to 10 mice/group). Statistical analysis was implemented by performing a one-way analysis of variance (one-way ANOVA) followed by a least significant difference test (Fisher LSD test). In FIG. 8, "*" and "***" show that a significant difference was observed at "p<0.05" and "p<0.001," respectively, as compared to the group administered DSS and saline.

As a result, a significant deterioration of the colonic inflammation score was observed in the mice of the "DSS+saline" group as compared to the mice of the "control" group. Furthermore, a significant improvement of the colonic inflammation score was observed in the "DSS+R-ketamine" group as compared to the "DSS+5-ASA" group.

Experimental Example 10

(Evaluation of Inflammatory Cytokines in Blood)

Inflammatory cytokines in plasma collected from the mice of each group on the 15th day from the start of the experiment in Experimental Example 7 were quantified. Interleukin (IL)-6 was quantified as the inflammatory cytokine. IL-6 was quantified by ELISA method using a commercially available kit.

Figure 9:
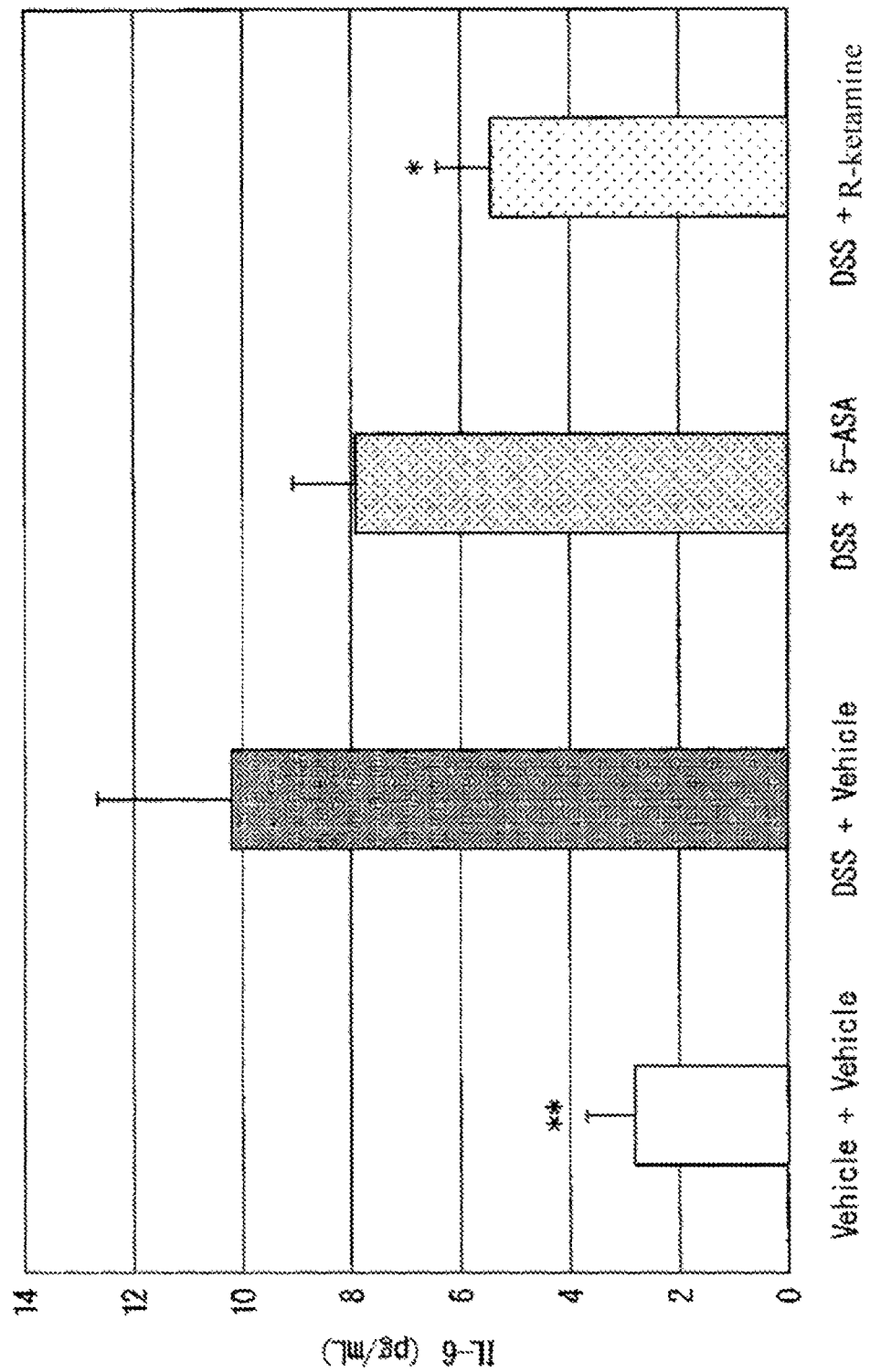
FIG. 9 A graph showing the results of Experimental Example 10.

FIG. 9 is a graph showing the results of quantifying IL-6 in blood. In FIG. 9, "Vehicle+Vehicle" shows the results of the mice in the control group, "DSS+Vehicle" shows the results of the mice in the group administered DSS and saline, "DSS+5-ASA" shows the results of the mice in the group administered DSS and 5-ASA, and "DSS+R-ketamine" shows the results of the mice in the group administered DSS and R-ketamine.

The data are represented by mean±standard error (n=8 to 10 mice/group). Statistical analysis was implemented by performing a one-way analysis of variance (one-way ANOVA) followed by a least significant difference test (Fisher LSD test). In FIG. 9, "*" and "**" show that significant differences were observed at "p<0.05" and "p<0.01," respectively, as compared to the "DSS+saline" group.

As a result, a significant increase of IL-6 concentration in blood was observed in the mice of the "DSS+saline" group as compared to the mice of the "control" group. Furthermore, a significant decrease of IL-6 concentration in blood was not observed in the "DSS+5-ASA" group. On the other hand, a significant decrease of IL-6 concentration in blood was observed in the "DSS+R-ketamine" group.

From the results of Experimental Examples 7 to 10, it was revealed that intraperitoneal administration of a 10 mg/kg dose of R-ketamine shows a significant therapeutic effect in DSS-treated mice, the ulcerative colitis animal model. In contrast to this, intraperitoneal administration of a 50 mg/kg dose of 5-ASA had an extremely weak therapeutic effect in the ulcerative colitis animal model.

Experimental Example 11

(Examination of the Effects of Administration of R-Ketamine and its Metabolite in Social Defeat Stress Model Mice)

R-ketamine and a metabolite of R-ketamine were administered to mice having depressive symptoms (hereinafter sometimes referred to as "social defeat stress mice"), prepared in the same way as Experimental Example 5, and the effects thereof were examined. R-ketamine hydrochloride prepared in the same way as Experimental Example 1 was used as R-ketamine. Furthermore, hydrochloride of 2R,6R-hydroxynorketamine (2R, 6R-HNK hydrochloride), which is the end product of R-ketamine, was used as the metabolite of R-ketamine. R-ketamine hydrochloride and 2R,6R-HNK hydrochloride were used after dissolving in saline.

Figure 10:
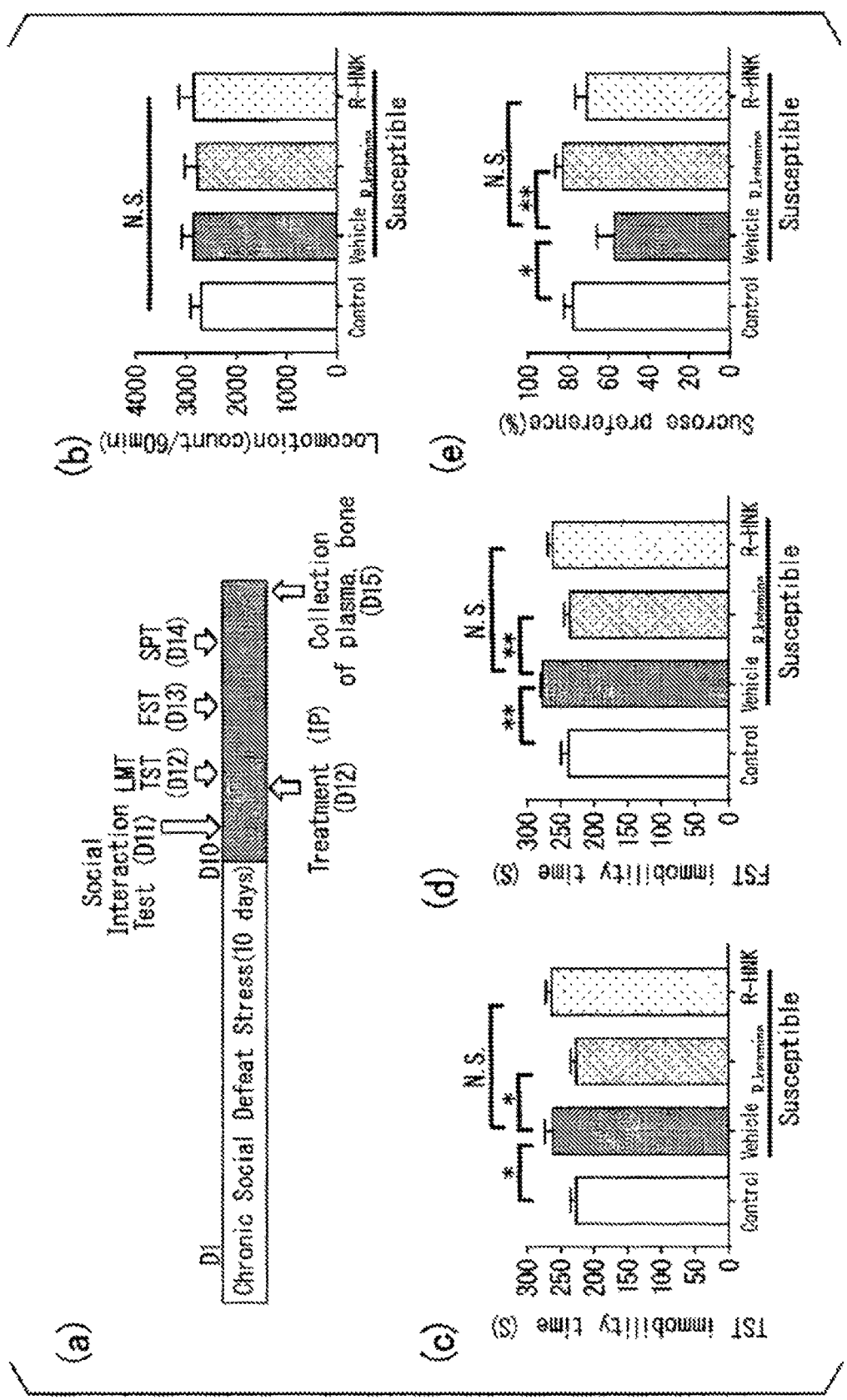
FIG. 10 (a) is a schematic diagram describing the experimental schedule of Experimental Example 11. (b) to (e) are graphs showing the results of the behavioral rating of Experimental Example 11.

FIG. 10 (a) is a schematic diagram describing an experimental schedule. R-ketamine (10 mg/kg body weight), 2R,6R-HNK (10 mg/kg body weight), or saline (10 mL/kg body weight) was intraperitoneally administered once to social defeat stress mice on the 12th day (D12); the day on which mice were first subjected to social defeat stress is the considered to be the 1st day (D1). Furthermore, C57/B6 male mice not subjected to "social defeat stress" were used as control mice. Saline (10 mL/kg body weight) was intraperitoneally administered once to control mice. Subsequently, measurement of momentum (LMT) and a tail suspension test (TST) were performed on the same 12th day (D12), the forced swimming test (FST) was performed on the same 13th day (D13), and a sucrose preference test (SPT) was performed on the same 14th day (D14).

Three days after administration (D15) of saline, R-ketamine, or 2R,6R-HNK, each mouse was anesthetized by inhalation of isoflurane. Subsequently, blood was collected and immediately centrifuged to obtain plasma. Plasma was stored in a freezer at −80° C. until measurement. Furthermore, the femur was collected for bone density measurement.

Subsequently, the concentrations of osteoprotegerin (Osteoprotegerin, hereinafter referred to as "OPG"), RANKL, and osteopontin (osteopontin, hereinafter referred to as "OPN") in each plasma were measured using an ELISA kit (R&D Systems, Inc.).

Furthermore, the bone density of the femur was measured using an X-ray CT for laboratory animals (Hitachi Aloka Medical, Ltd., LaTheta LCT-200).

FIG. 10 (b) to (e) are graphs showing the results of the behavioral rating. FIG. 10 (b) is the measurement results of momentum. FIG. 10 (c) is the measurement results of the tail suspension test. FIG. 10 (d) is the measurement results of the forced swimming test. FIG. 10 (e) is the measurement results of the sucrose preference test.

In FIG. 10 (b) to (e), the data are shown by mean±standard error (n=10 mice/group), "Control" shows the results of the control mice, "Susceptible" shows the results of the mice that exhibited depressive symptoms due to social defeat stress, "Vehicle" shows the results of the mice administered saline, "R-ketamine" shows the results of the mice administered R-ketamine, and "R-NHK" shows the results of the mice administered 2R,6R-HNK. Furthermore, "*" and "**" show there is a significant difference at "p<0.05" and "p<0.01," respectively, as compared to the social defeat stress mouse group administered saline. Moreover, "N. S." showed no significant difference. Statistical analysis was implemented by performing a one-way analysis of variance followed by a least significant difference test.

As a result, as shown in FIG. 10 (c) to (e), it was revealed that when administering R-ketamine to social defeat stress mice, a significantly higher antidepressant effect is exhibited as compared to when saline was administered to social defeat stress mice. On the other hand, it was revealed that even when 2R,6R-HNK is administered to social defeat stress mice, no antidepressant effect is exhibited.

Figure 11:
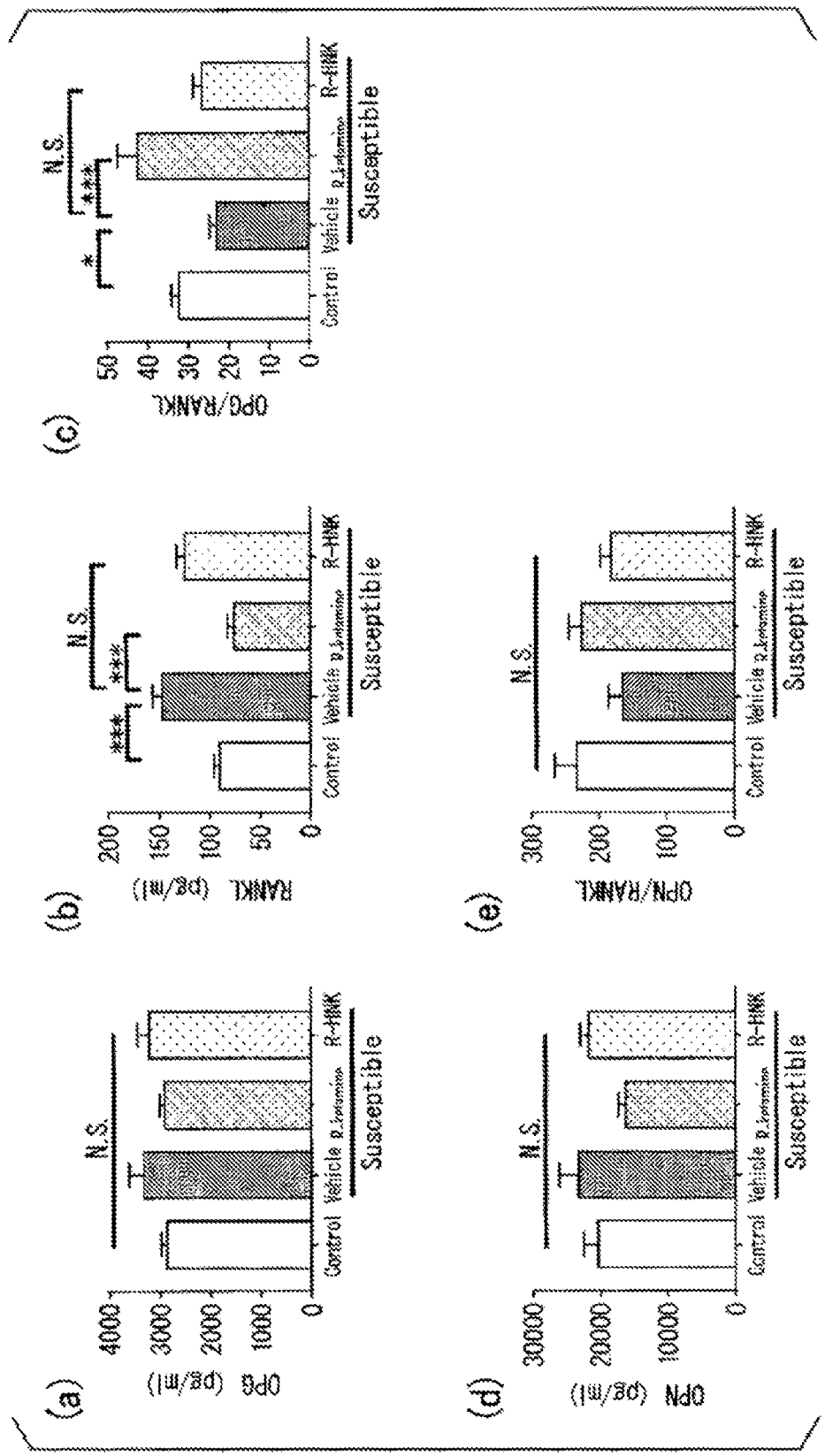
FIG. 11 (a) to (e) are graphs showing measurement results of osteoprotegerin (OPG), RANKL, and osteopontin (OPN) in Experimental Example 11.

FIG. 11 (a) to (e) are graphs showing the measurement results of OPG, RANKL, and OPN. FIG. 11 (a) shows the measurement results of OPG, FIG. 11 (b) shows the measurement results of RANKL, FIG. 11 (c) shows the OPG/RANKL ratio calculated based on the results of FIGS. 11 (a) and (b), FIG. 11 (d) shows the measurement results of OPN, and FIG. 11 (e) shows the OPN/RANKL ratio calculated based on the results of FIGS. 11 (b) and (d).

In FIG. 11 (a) to (e), the data are shown by mean±standard error (n=10 mice/group), "Control" shows the results of the control mice, "Susceptible" shows the results of the mice that exhibited depressive symptoms due to social defeat stress, "Vehicle" shows the results of the mice administered saline, "R-ketamine" shows the results of the mice administered R-ketamine, and "R-NHK" shows the results of the mice administered 2R,6R-HNK. Furthermore, "*" and "***" show there is a significant difference at "p 0.05" and "p<0.001," respectively, as compared to the social defeat stress mouse group administered saline. Furthermore, "N.S." showed no significant difference. Statistical analysis was implemented by performing a one-way analysis of variance followed by a least significant difference test.

As a result, as shown in FIG. 11 (b), it was revealed that the social defeat stress mice have significantly higher RANKL concentration in plasma as compared to the control mice. Furthermore, it was revealed that when administering R-ketamine to social defeat stress mice, RANKL concentration in plasma was significantly decreased as compared to when saline was administered to social defeat stress mice. On the other hand, even when 2R,6R-NHK was administered to social defeat stress mice, a significant change to RANKL concentration in plasma was not observed as compared to when saline was administered to social defeat stress mice. As shown in FIG. 11 (c), the OPG/RANKL ratio in the social defeat stress mice significantly increased due to R-ketamine administration; however, a significant change was not observed in those administered 2R,6R-HNK. Note that as shown in FIGS. 11 (d) and (e), no significant difference in OPN concentration in plasma and the OPN/RANKL ratio was observed.

As described above, bone homeostasis is maintained by a delicate balance between bone resorption by osteoclasts and bone formation by osteoblasts. The OPG/RANKL ratio is a marker used as an indicator of the balance between bone formation and bone resorption. As shown in FIG. 11 (c), it was revealed that the OPG/RANKL ratio of the social defeat stress mice administered saline was significantly decreased as compared to the control mice. A low OPG/RANKL ratio shows that bone destruction and resorption tend to be superior to bone formation.

Moreover, it was revealed that when administering R-ketamine to social defeat stress mice, the OPG/RANKL was significantly increased as compared to when saline was administered to social defeat stress mice. On the other hand, even when 2R,6R-HNK, a metabolite of R-ketamine, was administered to social defeat stress mice, a significant change to the OPG/RANKL ratio was not observed as compared to when saline was administered to social defeat stress mice.

From the above results, it was revealed that the administration of R-ketamine is able to restore an abnormally high expression of RANKL to a normal value. On the other hand, no therapeutic effect was observed for 2R,6R-HNK, a metabolite of R-ketamine. This result shows that R-ketamine is useful as a preventive or therapeutic drug for bone diseases, and it is considered to be an effect of R-ketamine itself, rather than the metabolite.

Figure 12:
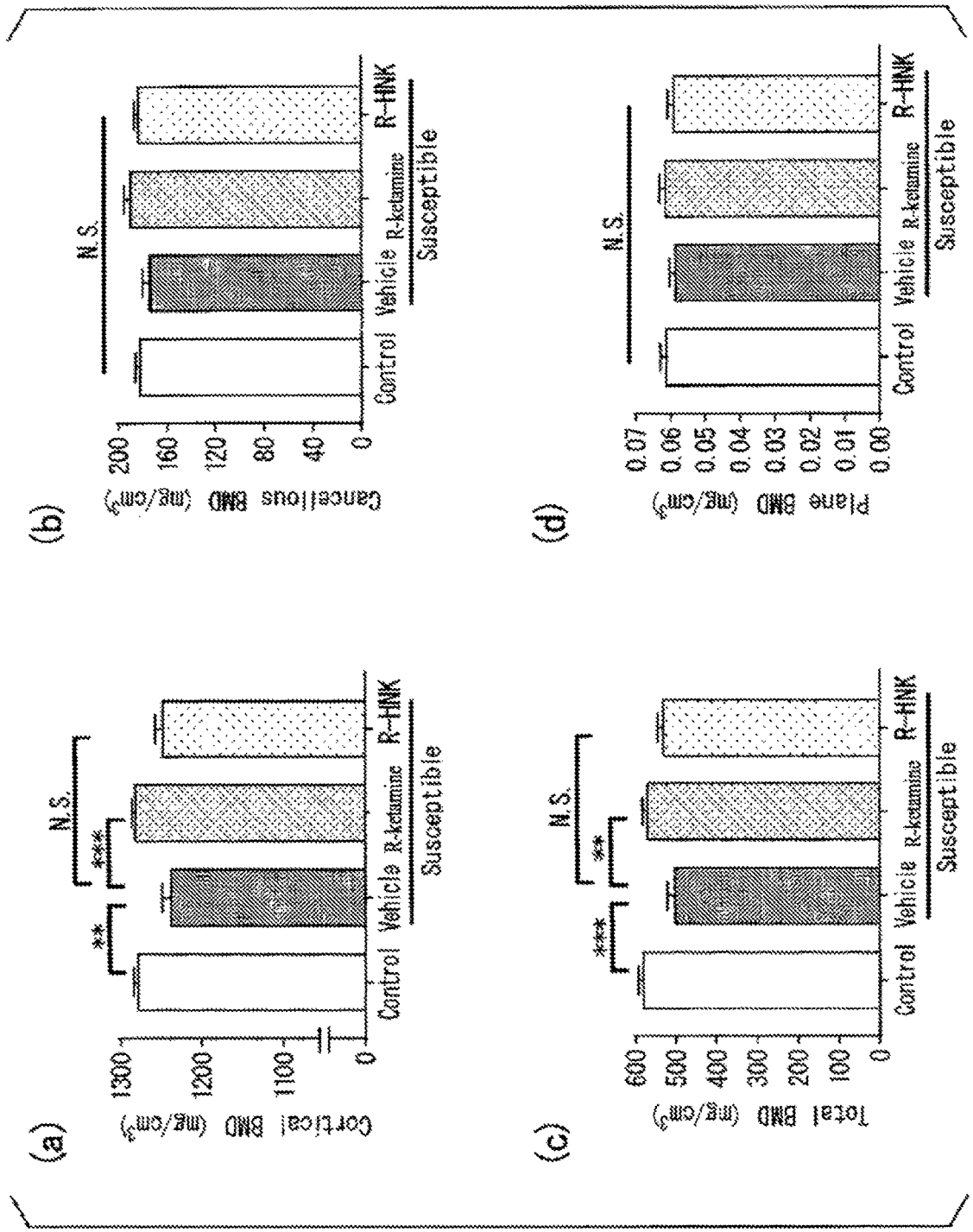
FIG. 12 (a) to (d) are graphs showing the measurement results of bone density in Experimental Example 11.

FIG. 12 (a) to (d) are graphs showing the measurement results of bone density. FIG. 12 (a) is a graph showing the results of cortical bone density, FIG. 12 (b) is a graph showing the results of cancellous bone density, FIG. 12 (c) is a graph showing the results of total bone density, and FIG. 12 (d) is a graph showing the results of plane bone density.

As a result, as shown in FIGS. 12 (a) and (c), it was revealed that cortical bone density and total bone density of the social defeat stress mice were significantly lower as compared to the control mice. Furthermore, it was revealed that when administering R-ketamine to social defeat stress mice, cortical bone density and total bone density were significantly improved as compared to when saline was administered to social defeat stress mice.

On the other hand, when administering 2R,6R-HNK to social defeat stress mice, no significant change in cortical bone density and total bone density was observed as compared to when saline was administered to social defeat stress mice. Furthermore, as shown in FIGS. 12 (b) and (d), no difference in cancellous bone density and plane bone density was observed between the 4 groups.

Experimental Example 12

(Examination 1 of R-ketamine Administration on Osteoporosis Model Animals)

Many studies have reported that the blood of osteoporosis patients has high concentrations of RANKL, and that a human anti-RANKL monoclonal antibody preparation (denosumab) is used as a therapeutic drug. In the present Experimental Example, sRANKL-administered mice were used as a model animal for osteoporosis, and the effect of R-ketamine was examined.

sRANKL (soluble RANKL, Oriental Yeast Co., Tokyo, Japan) was intraperitoneally administered to 10-week-old female ddY mice (Japan SLC, Inc., Hamamatsu, Japan) to prepare an osteopenia model, then the effect of R-ketamine was examined. Note that sRANKL is an abbreviation of soluble RANKL. R-ketamine hydrochloride prepared in the same way as Experimental Example 1 was used as R-ketamine, and used after dissolving in saline. Furthermore, mice to which physiological saline was administered instead of sRANKL were used as control mice.

R-ketamine (10 mg/kg) was intraperitoneally administered 30 minutes before administration of sRANKL (1 mg/kg), and 24 hours and 48 hours after. Twenty-four hours after the final administration, each mouse was anesthetized by inhalation of isoflurane. Subsequently, the femur was collected for bone density measurement. Bone density of the femur was measured using an X-ray CT for laboratory animals (Hitachi Aloka Medical, Ltd., LaTheta LCT-200). Statistical analysis was implemented by performing a one-way analysis of variance followed by a least significant difference test.

Figure 13:
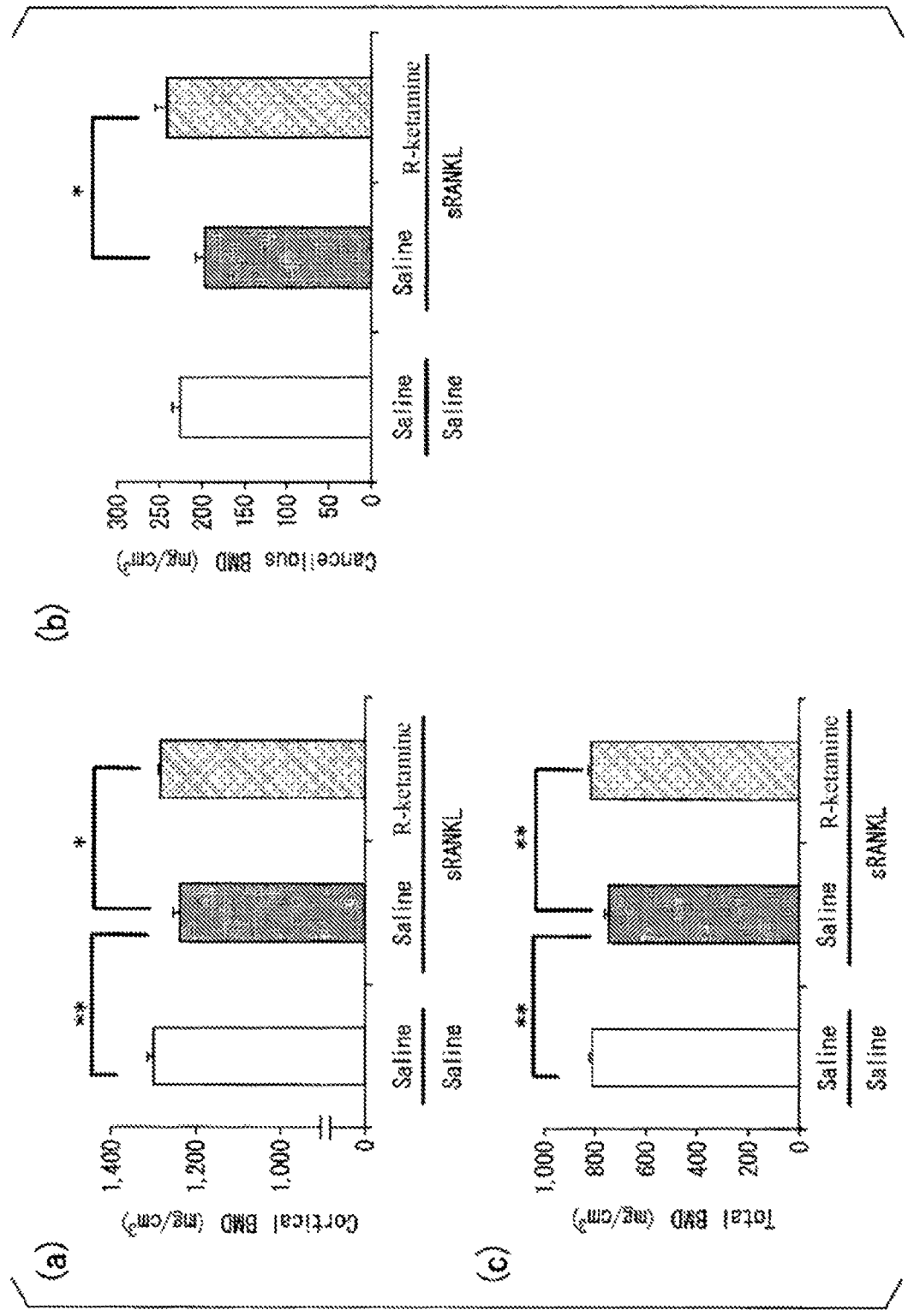
FIG. 13 (a) to (c) are graphs showing the measurement results of bone density in Experimental Example 12.

FIG. 13 (a) to (c) are graphs showing the measurement results of bone density. FIG. 13 (a) is a graph showing the results of cortical bone density, FIG. 13 (b) is a graph showing the results of cancellous bone density, and FIG. 13 (c) is a graph showing the results of total bone density. In FIG. 13 (a) to (c), "Saline" shows the results of the mice administered saline, "sRANKL" shows the results of the mice administered sRANKL, and "R-ketamine" shows the results of the mice administered R-ketamine. Furthermore "*" and "**" show that a significant difference was observed at "p<0.05" and "p<0.01," respectively, as compared to mice administered sRANKL and saline.

As a result, as shown in FIGS. 13 (a) and (c), it was revealed that cortical bone density and total bone density of the mice administered sRANKL were significantly lower as compared to the control mice. Furthermore, it was revealed that when administering R-ketamine to sRANKL-administered mice, cortical bone density and total bone density were significantly improved as compared to when saline was administered. Moreover, as shown in FIG. 13 (b), it was revealed that cancellous bone density of mice administered sRANKL was significantly increased when administering R-ketamine.

From the above results, it was revealed that the administration of R-ketamine is able to improve a decrease in bone density of the femurs of mice administered sRANKL. This result shows that R-ketamine is useful as a preventive or therapeutic agent for bone diseases.

Experimental Example 13

(Examination 2 of R-ketamine Administration on Osteoporosis Model Animals)

The effect of R-ketamine was examined using ovariectomized mice as a model animal for osteoporosis.

8-week-old female ddY mice (Japan SLC, Inc., Hamamatsu, Japan) were anesthetized by inhalation of isoflurane, then a sham operation or ovariectomy operation was performed (Wednesday). The next day (Thursday), saline (10 mL/kg) or R-ketamine (10 mg/kg) was intraperitoneally administered. Thereafter, administration of saline or R-ketamine was repeated on Monday and Thursday, and 6 weeks after the surgery each mouse was anesthetized by inhalation of isoflurane. Subsequently, the femur was collected for bone density measurement.

Bone density of the femur was measured using an X-ray CT for laboratory animals (Hitachi Aloka Medical, Ltd., LaTheta LCT-200). Statistical analysis was implemented by performing a one-way analysis of variance followed by a least significant difference test.

Figure 14:
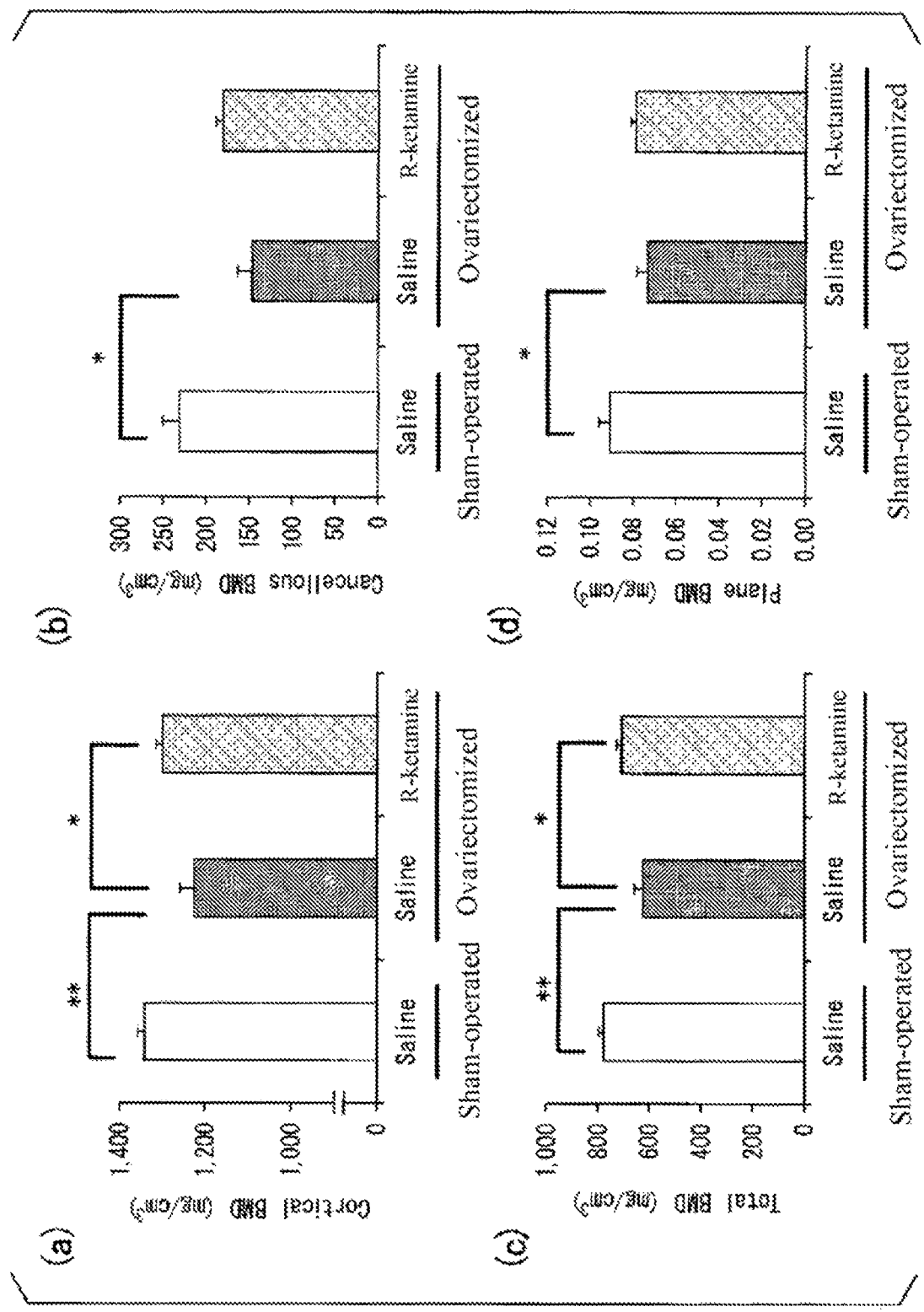
FIG. 14 (a) to (d) are graphs showing the measurement results of bone density in Experimental Example 13.

FIG. 14 (a) to (d) are graphs showing the measurement results of bone density. FIG. 14 (a) is a graph showing the results of cortical bone density, FIG. 14 (b) is a graph showing the results of cancellous bone density, FIG. 14 (c) is a graph showing the results of total bone density, and FIG. 14 (d) is a graph showing the results of plane bone density.

In FIG. 14 (a) to (d), "Saline" shows the results of the mice administered saline, and "R-ketamine" shows the results of the mice administered R-ketamine. Furthermore "*" and "**" show that a significant difference was observed at "p<0.05" and "p<0.01," respectively, as compared to mice that underwent ovariectomy surgery and were administered saline.

As a result, as shown in FIGS. 14 (a) and (c), it was revealed that cortical bone density, cancellous bone density, total bone density, and plane bone density of ovariectomized mice were significantly lower as compared to the sham-operated mice. Furthermore, it was revealed that when administering R-ketamine to ovariectomized mice, cortical bone density and total bone density were significantly improved as compared to when saline was administered. Moreover, as shown in FIGS. 14 (b) and (d), it was revealed that cancellous bone density and plane bone density of ovariectomized mice tended to increase along with R-ketamine administration, but it was not statistically significant.

From the above results, it was revealed that administration of R-ketamine enables an improvement of a decrease in bone density of the femur of ovariectomized mice. This result further supports the fact that R-ketamine is useful as a preventive or therapeutic agent for bone diseases.

INDUSTRIAL APPLICABILITY

According to the present invention, it is possible to provide a preventative or therapeutic agent and pharmaceutical composition for an inflammatory disease or a bone disease.

The invention claimed is:

1. A method of preventing or treating ulcerative colitis or Crohn's disease in a subject in need thereof, comprising administering to the subject a composition comprising a compound of formula (1) or a pharmacologically acceptable salt thereof:

[Formula 1]

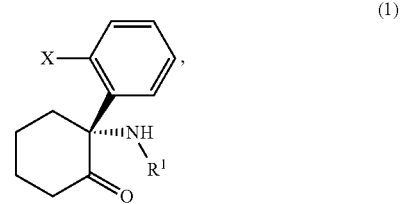

(1)

wherein the composition comprises less than 0.15 mol % of a compound of formula (3) compared to an amount of the compound of formula (1):

[Formula 3]

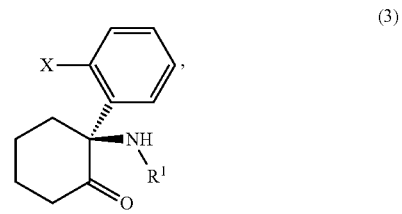

(3)

wherein in formula (1) and formula (3), X represents a hydrogen atom, a halogen atom, or a $C_1$-$C_{10}$ alkyl group that may be substituted; $R^1$ represents a $C_1$-$C_{10}$ alkyl group that may be substituted, a $C_1$-$C_{10}$ alkenyl group that may be substituted, or a $C_6$-$C_{14}$ aryl group that may be substituted; and one or more hydrogen atoms may be substituted for deuterium atoms.

2. The method according to claim 1, wherein the compound of formula (1) is represented by formula (2) or a pharmacologically acceptable salt thereof:

[Formula 2]

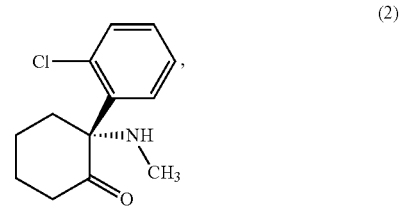

(2)

and wherein the compound of formula (3) is represented by formula (4) or a pharmacologically acceptable salt thereof:

[Formula 4]

(4)

3. The method of claim 1, wherein the composition is a pharmaceutical composition comprising a pharmacologically acceptable carrier.

4. The method of claim 1, wherein the composition does not contain the compound of formula (3).

5. The method of claim 2, wherein the composition does not contain the compound of formula (4).

6. The method of claim 1, wherein the composition is formulated for oral, nasal, intravenous, subcutaneous or intramuscular administration.

7. The method of claim 1, wherein the composition is in the form of a liquid, solution, suspension, powder, tablet, coated tablet, capsule, troche, cream, suppository, gel, patch, liniment or aerosol.

8. The method of claim 1, comprising administering a therapeutically effective amount of the composition to the subject.

9. The method of claim 8, wherein the therapeutically effective amount is about 0.01 mg/day to about 1,000 mg/day.

10. The method of claim 8, wherein the therapeutically effective amount is about 0.1 mg/day to about 500 mg/day.

11. The method of claim 8, wherein the therapeutically effective amount is about 0.1 mg/day to about 100 mg/day.

12. The method of claim 1, wherein the compound of formula (1) or a pharmacologically acceptable salt thereof is R-ketamine.

13. The method of claim 1, wherein the compound of formula (3) or a pharmacologically acceptable salt thereof is S-ketamine.

14. The method of claim 4, wherein one or more hydrogen atoms in formula (1) are substituted for deuterium atoms.

* * * * *